(12) United States Patent
Fessler et al.

(10) Patent No.: US 9,211,302 B2
(45) Date of Patent: Dec. 15, 2015

(54) MODULATION OF LRCH4 ACTIVITY AND THERAPEUTIC APPLICATION THEREOF

(75) Inventors: Michael B. Fessler, Cary, NC (US); Jim J. Aloor, Chapel Hill, NC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 23 days.

(21) Appl. No.: 13/980,097

(22) PCT Filed: Jan. 17, 2012

(86) PCT No.: PCT/US2012/021538
§ 371 (c)(1),
(2), (4) Date: Sep. 24, 2013

(87) PCT Pub. No.: WO2012/099871
PCT Pub. Date: Jul. 26, 2012

(65) Prior Publication Data
US 2014/0037653 A1    Feb. 6, 2014

Related U.S. Application Data
(60) Provisional application No. 61/433,491, filed on Jan. 17, 2011.

(51) Int. Cl.
| | | |
|---|---|---|
| A61K 31/713 | (2006.01) | |
| C12N 15/113 | (2010.01) | |
| A61K 38/17 | (2006.01) | |
| A61K 39/395 | (2006.01) | |

(52) U.S. Cl.
CPC ........... *A61K 31/713* (2013.01); *A61K 38/1709* (2013.01); *A61K 39/3955* (2013.01); *C12N 15/113* (2013.01); *C12N 15/1138* (2013.01); *C12N 2310/14* (2013.01); *C12N 2310/531* (2013.01)

(58) Field of Classification Search
USPC ............. 435/6.1, 6.11, 455, 91.1, 91.31, 458; 424/9.1; 514/1, 2, 44; 536/23.1, 24.5
See application file for complete search history.

(56) References Cited

U.S. PATENT DOCUMENTS

| | | | |
|---|---|---|---|
| 4,735,210 | A | 4/1988 | Goldenberg |
| 4,683,195 | B1 | 11/1990 | Mullis et al. |
| 4,683,202 | B1 | 11/1990 | Mullis |
| 5,101,827 | A | 4/1992 | Goldenberg |
| 5,102,990 | A | 4/1992 | Rhodes |
| 5,194,594 | A | 3/1993 | Khawli et al. |
| 5,530,101 | A | 6/1996 | Queen et al. |
| 5,585,089 | A | 12/1996 | Queen et al. |
| RE35,500 | E | 5/1997 | Rhodes |
| 5,648,471 | A | 7/1997 | Buttram et al. |
| 5,693,761 | A | 12/1997 | Queen et al. |
| 5,693,792 | A | 12/1997 | Torii et al. |
| 5,697,902 | A | 12/1997 | Goldenberg |
| 5,703,057 | A | 12/1997 | Johnston et al. |
| 5,714,350 | A | 2/1998 | Co et al. |
| 5,733,743 | A | 3/1998 | Johnson et al. |
| 5,777,085 | A | 7/1998 | Co et al. |

FOREIGN PATENT DOCUMENTS

| | | |
|---|---|---|
| WO | WO 94/29444 A1 | 12/1994 |
| WO | WO 97/38137 A1 | 10/1997 |

OTHER PUBLICATIONS

U.S. Appl. No. 08/759,620, filed Dec. 3, 1996, Jakobovits et al.
Bernstein et al.; "Role for a bidentate ribonuclease in the initiation step of RNA interference"; Nature; vol. 409; Jan. 2001; p. 363-366.
Tuschl; "Expanding small RNA interference"; Nat. Biotechnol.; vol. 20; May 2002; p. 446-448.
Yu et al.; "RNA interference by expression of short-interfering RNAs and hairpin RNAs in mammalian cells"; Proc. Natl. Acad. Sci.; vol. 99 No. 9; Apr. 2002; p. 6047-6052.
Sui et al.; "A DNA vector-based RNAi technology to suppress gene expression in mammalian cells"; Proc. Natl. Acad. Sci.; vol. 99 No. 8; Apr. 2002; p. 5515-5520.
Paddison et al.; "Short hairpin RNAs (shRNAs) induce sequence-specific silencing in mammalian cells"; Genes & Development; vol. 16; 2002; p. 948-58.
Brummelkamp et al.; "A System for Stable Expression of Short Interfering RNAs in Mammalian Cells"; Science; vol. 296; Apr. 2002; p. 550-553.
Miyagashi et al.; "U6 promoter-driven siRNAs with four uridine 3' overhangs efficiently suppress targeted gene expression in mammalian cells"; Nature Biotechnology; vol. 19; May 2002; p. 497-500; 2002.
Grishok et al.; "Genes and Mechanisms Related to RNA Interference Regulate Expression of the Small Temporal RNAs that Control C. elegans Developmental Timing"; Cell; vol. 106 Jul. 2001; p. 23-34.
Hutvagner et al.; "A Cellular Function for the RNA-Interference Enzyme Dicer in the Maturation of the let-7 Small Temporal RNA"; Science; vol. 293; Aug. 2001; p. 834-838.
Ketting et al.; "Dicer functions in RNA interference and in synthesis of small RNA involved in developmental timing in C. elegans"; Genes & Development; vol. 15; 2001; p. 2654-2659.
Zeng et al.; "Both Natural and Designed Micro RNAs Can Inhibit the Expression of Cognate mRNAs When Expressed in Human Cells"; Molecular Cell; vol. 9; Jun. 2002; p. 1327-1333.
McManus et al.; "Gene silencing using micro-RNA designed hairpins"; RNA; vol. 8; 2002; p. 842-850.
Denhardt; "Mechanism of Action of Antisense RNA: Sometime Inhibition of Transcription, Processing, Transport, or Translation"; Annals NY Academy of Sciences; vol. 660; Oct. 1992; p. 70-76.
Nellen et al.; "What makes an mRNA anti-sense-itive?"; TIBS; vol. 18; Nov. 1993; p. 419-423.
Varga et al.; "Antisense strategies: functions and applications in immunology"; Immunology Letters; vol. 69; 1999; p. 217-224.
Neilsen; "Applications of peptide nucleic acids"; Current Opinion Biotechnology; vol. 10; 1999; p. 71-75.

(Continued)

*Primary Examiner* — Jane Zara

(57) ABSTRACT

Disclosed herein are methods for altering cellular functions and processes by modulating the activity of Lrch4. Corresponding compositions that may be used in carrying out the described methods are also disclosed as are related methods of treatment for relevant diseases and physiological states.

10 Claims, 20 Drawing Sheets

(56) References Cited

OTHER PUBLICATIONS

Woolf et al.; "The stability, toxicity and effectiveness of unmodified and phosphorothioate antisense oligodeoxynucleotides in Xenopus oocytes and embroys"; Nucleic Acids Research; vol. 18 No. 7; 1990; p. 1763-1769.

Cotten et al.; "Ribozyme mediated destruction of RNA in vivo"; The EMBO Journal; vol. 8 No. 12; 1989; p. 3861-3866.

Usman et al.; "Hammerhead ribozyme engineering"; Current Opinion in Structural Biology; vol. 1; 1996; p. 527-533.

Liu et al.; "Supercoiling of the DNA template during transcription"; Proc. Natl. Acad. Sci.; vol. 84; 1987; p. 7024-7027.

Liu et al.; "Production of a Mouse-Human Chimeric Monoclonal Antibody to CD20 With Potent Fc-Dependent Biologic Activity"; The Journal of Immunology; vol. 139 No. 10; Nov. 1987; p. 3521-3526.

Wu et al.; Synthetic Oligodeoxynucleotides for Analyses of DNA Structure and Function; Progress Nucleic Acid Research Molecular Biology; vol. 21; 1978; p. 101-141.

Lathe; "Synthetic Oligonucleotide Probes Deduced from Amino Acid Sequence Data: Theoretical and Practical Considerations"; J. Mol. Biol.; vol. 183; 1985; p. 1-12.

Belagaje et al.; "Total Synthesis of a Tyrosine Suppressor Transfer RNA Gene"; The Journal of Biological Chemistry; vol. 254 No. 13; Jul. 1979; p. 5765-5780.

Khorana; "Total Synthesis of a Gene"; Science; vol. 203; Feb. 1979; p. 614-625.

Hsu et al.; "Cloning of cDNAs for human aldehyde dehydrogenases 1 and 2"; Proc. Natl. Acad. Sci.; vol. 82 No. 11; Jun. 1985; p. 3771-3775.

Suzuki et al.; "Complete amino acid sequence of human vitronectin deduced from cDNA. Similarity of cell attachment sites in vitronectin and fibronectin"; The EMBO Journal; vol. 4 No. 10; 1985; p. 2519-2524.

Walter et al.; "Cloning of the human estrogen receptor cDNA"; Proc. Natl. Acad. Sci.; vol. 82 No. 23; Dec. 1985; p. 7889-7893.

Pennica et al.; "Cloning and expression of human tissue-type plasminogen activator cDNA in E. coli"; Nature; vol. 301; Jan. 1983; p. 214-221.

Marks et al.; "Human Antibody Fragments Specific for Human Blood Group Antigens from a Phage Display Library"; Bio/Technology; vol. 11; Oct. 1993; p. 1145-1149.

Green et al.; "Antigen-specific human monoclonal antibodies from mice engineered with human Ig heavy and light chain YACs"; Nature Genetics; vol. 7; May 1994; p. 13-21.

Mendez et al.; "Functional transplant of megabase human immunoglobulin loci recapitulates human antibody response in mice"; Nature Genetics; vol. 15; Feb. 1997; p. 146-156.

Green et al.; "Regulation of B Cell Development by Variable Gene Complexity in Mice Reconstituted with Human Immunoglobulin Yeast Artificial Chromosomes"; Journal of Experimental Medicine; vol. 188 No. 3; Aug. 1998; p. 483-495.

Winter et al.; "Humanized antibodies"; Immunology Today; vol. 14 Issue 6; Jun. 1993; p. 243-246.

Wright et al.; "Genetically Engineered Antibodies: Progress and Prospects"; Critical Reviews in Immunology; vol. 12; 1992; p. 125-168.

Okayama et al.; "A cDNA Cloning Vector That Permits Expression of cDNA Inserts in Mammailian Cells"; Molecular and Cellular Biology; vol. 3 No. 2; Feb. 1983; p. 280-289.

Gorman et al.; "The Rous sarcoma virus long terminal repeat is a strong promoter when introduced into a variety of eukaryotic cells by DNA-mediated transfection"; Proc. Natl. Acad. Sci. USA; vol. 79 No. 22; Nov. 1982; p. 6777-6781.

Grosschedl et al.; Cell-Type Specificity of Immunoglobulin Gene Expression is Regulated by at Least Three DNA Sequence Elements; Cell; vol. 41; Jul. 1985; p. 885-897.

Parmley et al.; "Antibody-selectable filamentous fd phage vectors: affinity purification of target genes"; Gene; vol. 73; 1988; p. 305-318.

Scott; "Discovering peptide ligands using epitope libraries"; TIBS; vol. 17; Jul. 1992; p. 241-245.

Cwirla et al.; "Peptides on phage: A vast library of peptides for identifying ligands"; Proc. Natl. Acad. Sci. USA; vol. 87; Aug. 1990; p. 6378-6382.

Russell et al.; "Retroviral vectors displaying functional antibody fragments"; Nucleic Acids Research; vol. 21 No. 5; 1993; p. 1081-1085.

Hoogenboom et al.; "Building Antibodies from their Genes"; Immunological Reviews; No. 130; 1992; p. 42-68.

Chiswell et al.; "Phage antibodies: will new "coliclonal" antibodies replace monoclonal antibodies?"; Trends in Biotechnology; vol. 10; 1992; p. 80-84.

Fanger et al.; "Production and Use of Anti-FcR Bispecific Antibodies"; ImmunoMethods; vol. 4; Feb. 1994; p. 72-81.

Ill et al.; "Design and construction of a hybrid immunoglobulin domain with properties of both heavy and light chain variable regions"; Protein Engineering; vol. 10 No. 8; 1997; p. 949-557.

Martin et al.; "The affinity-selection of minibody polypeptide inhibitor of human interleukin-6"; The EMBO Journal; Vo. 13 No. 22; 1994; p. 5303-5309.

Holliger et al.; "Diabodies": Small bivalent and bispecific antibody fragments; Proc. Natl. Acad. Sci. USA; vol. 90; Jul. 1993; p. 6444-6448.

Traunecker et al.; "Bispecific single chain molecules (Janusins) target cytotoxic lymphocytes on HIV infected cells"; The EMBO Journal; vol. 10 No. 12; 1991; p. 3655-3659.

Traunecker et al.; "Janusin: New Molecular Design for Bispecific Reagents"; Int. J. Cancer Supplement; vol. 7; 1992; p. 51-52.

Vitetta et al.; "Immunotoxins: magic bullets or misguided missles?"; Immunologytoday; vol. 14 No. 6; 1993; p. 252-259.

Junghans et al.; "Antiobody-Based Immunotherapies for Cancer"; Cancer Chemotherapy and Biotherapy; $2^{nd}$ Edition; Chapter 28; 1996; p. 655-689.

Houghten et al.; "The Use of Synthetic Peptide Combinatorial Libraries for the Identification of Bioactive Peptides"; BioTechniques; vol. 13 No. 3; 1992; p. 412-421.

Houghten; "General method for the rapid solid-phase synthesis of large numbers of peptides: Specificity of antigen-antibody interaction at the level of individual amino acids"; Proc. Natl. Acad. Sci. USA; vol. 82; 1985; p. 5131-5135.

Pinilla et al.; "Rapid identification of high affinity peptide ligands using positional scanning synthetic peptide combinatorial libraries"; BioTechniques; vol. 13 No. 6; 1992; p. 901-905.

Blake et al.; "Evaluation of Peptide Libraries: An Iterative Strategy to Analyze the Reactivity of Peptide Mixtures with Antibodies"; BioConjugate Chem.; vol. 3; 1992; p. 510-513.

Scott et al; "Searching for Peptide Ligands with an Epitope Library"; Science; vol. 249 No. 4967; Jul. 1990; p. 386-390.

Felici et al.; "Selection of Antibody Ligands from a Large Library of Oligopeptides Expressed on a Multivalent Exposition Vector"; J. Mol. Biol.; vol. 222; 1991; p. 301-310.

Kuwabara et al.; "Efficient epitope mapping by bacteriophage A surface display"; Nature Biotechnology; vol. 15; Jan. 1997; p. 74-78.

Chen et al.; Intracellular Antibodies as a New Class of Therapeutic Molecules for Gene Therapy; Human Gene Therapy; vol. 5 No. 5; May 1994; p. 595-601.

Marasco; "Intrabodies: turning the humoral immune system outside in for intracellular immunization"; Gene Therapy; vol. 4; 1997; p. 11-15.

Fry et al.; "Specific, irreversible inactivation of the epidermal growth factor receptor and erbB2, by a new class of tyrosine kinase inhibitor"; Proc. Natl. Acad. Sci. USA; vol. 95; Sep. 1998; p. 12022-12027.

Hoffman et al.; "A Model of Cdc25 Phosphatase Catalytic Domain and Cdk-Interaction Surface Based on the Presence of a Rhodanese Homology Domain"; J. Mol. Biol.; vol. 282; 1998; p. 195-208.

Ginalski et al.; "Modelling of active forms of protein kinases: p38—a case study"; Acta Biochimica Polonica; vol. 44 No. 3; 1997; p. 557-564.

Joukov et al.; "Identification of CSK tyrosine phosphorylation sites and a tyrosine residue important for kinase domain structure"; Biochem J; vol. 322; 1997; p. 927-935.

(56) References Cited

OTHER PUBLICATIONS

Singh et al.; "Structure-Based Design of a Potent, Selective, and Irreversible Inhibitor of the Catalytic Domain of the erbB Receptor Subfamily of Protein Tyrosine Kinases"; J. Med. Chem; vol. 40; 1997; p. 1130-1135.

Mandel et al.; "ABGEN: A Knowledge-Based Automated Approach for Antibody Structure Modelin"; Nature Biotechnology; vol. 14; 1996; p. 323-328.

Monfardini et al.; "Rational Design, Analysis, and Potential Utility of GM-CSF Antagonists"; Proceeding of the Assoc. American Physicians; vol. 108 No. 6; 1996; p. 420-431.

Furet et al.; "Modelling study of protein kinase inhibitors: Binding mode of staurosporine and origin of the selectivity of CGP 52411"; Journal of Computer-Aided Molecular Design; vol. 9; Dec. 1995; p. 465-472.

Langer; "New Methods of Drug Delivery"; Science; Sep. 1990; vol. 249:1527-1533.

Hanes et al.; "New advances in microsphere-based single-dose vaccines"; Advanced Drug Delivery Reviews; vol. 28; 1997; p. 97-119.

Paul et al.; "Transdermal immunization with large proteins by means of ultradeformable drug carriers"; Eur. J. Immunol.; vol. 25; 1995; p. 3521-3524.

Cevc et al.; "Ultraflexible vesicles, Transfersomes, have an extremely low pore penetration resistance and transport therapeutic amounts of insulin across the intact mammalian skin"; Biochimica et Biophysica Acta; vol. 1368; 1998; p. 201-215.

Foussard et al; "LRCH Proteins: A Novel Family of Cytoskeletal Regulators"; PLoS One; Aug. 2010; vol. 5 Issue 8; 11 pages.

Takeda et al.; "Inhibition of Prolyl Hydroxylase Domain-Containing Protein Suppressed Lipopolysaccharide-Induced TNF-a Expression"; Arteriosclerosis, Thrombosis, and Vascular Biology; Sep. 2009; vol. 29 No. 12; 16 pages.

a.

b.

a.

b.

a.

b.

MODULATION OF LRCH4 ACTIVITY AND THERAPEUTIC APPLICATION THEREOF

CROSS-REFERENCE TO RELATED APPLICATIONS

This application is the national stage of PCT/US2012/021538, filed Jan. 17, 2012, which claims the benefit of priority to U.S. Provisional Patent Application Ser. No. 61/433,491, filed Jan. 17, 2011, the disclosures of which are incorporated herein by reference in their entireties.

TECHNICAL FIELD

The subject matter described herein relates to modulating cellular activity by altering the activity of Lrch4.

BACKGROUND

Leucine-rich repeat and calponin homology domain-containing protein 4 (Lrch4) is a single-spanning transmembrane protein that is encoded by the Lrch4 gene in humans. The human form of Lrch4 is 83% identical to murine Lrch4 and was identified in a proteomic screen of macrophage as being rapidly recruited to lipid rafts after LPS exposure. It is predicted to have 680 amino acids and have a molecular weight of 73 kDa.

Toll-like receptors (TLRs) are a type of pattern recognition receptors found in vertebrates and invertebrates—there are ten different varieties in humans all of which recognize different ligands. TLRs 1, 2, 4, 5, and 6 are expressed as cell surface receptors, while TLRs 3, 7 and 9 are expressed on internal cellular membranes. TLRs are categorized as pattern recognition receptors because they recognize conserved aspects microbial proteins, such as bacterial cell-surface lipopolysaccharides, or in the case of intracellular receptors, foreign nucleic acids. Not surprisingly, they play a central role in the innate immune response and are known to be involved in signaling pathways that control cytokine production. TLRs commonly function as dimers. While most TLRs appear to function as homodimers, TLR2 is known to form heterodimers with TLR1 and TLR6, although each of these dimers has a different ligand specificity. Cell signaling mediated by all TLRs other than TLR3 involves interacting with the accessory protein MyD88, a cytosolic adaptor which is known to activate the transcription factor NF-κB.

In addition, and in some instances because of, their role in innate immunity, TLRs are also known (or implicated) to play a significant role in certain diseases, such as sepsis; respiratory diseases (acute respiratory distress syndrome, asthma, and chronic obstructive pulmonary disease); autoimmune diseases (systemic lupus erythematosus and rheumatoid arthritis); inflammatory bowel syndrome; heart disease (acute coronary syndrome); cancer; metabolic syndrome; and atherosclerosis, to name a few. Because of the association of TLRs with disease, they are an attractive target for new therapeutics. See Hennessy et al., *Nature Reviews* 9:293 (2010).

SUMMARY

Disclosed herein are methods of modulating signaling in a cell by altering the activity of Lrch4. In some embodiments, cell signaling mediated by TLRs is modulated; however, in other embodiments non-TLR-mediated signaling, such as that mediated by PMA, is modulated. In some embodiments, Lrch4 activity is altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity.

Also disclosed are methods for modulating a cellular response to a TLR ligand by altering the activity of Lrch4 in a cell contacted with the ligand. In some embodiments, Lrch4 activity may be altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing the Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity.

The methods disclosed in this regard may be used to modulate one or more of a variety of cellular response, individually or in combination, to a TLR ligand. For example, in some embodiments, the cellular response that is modulated is cytokine expression. Cytokines that may be modulated by the methods described herein include, but are not limited to: tumor necrosis factor alpha (TNF-α), TNF-β, interferon alpha (IFN-α), IFN-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, or IL-35. In some embodiments, cytokine expression may be modulated such that cellular expression is reduced, while in other embodiments, expression may be increased. Furthermore, other cellular responses can be modulated by the methods described herein. For example, the function of cellular signaling proteins, adaptor proteins, or transcription factors, such as mitogen-activated protein (MAP) kinases, MyD88, or nuclear factor (NF)-κB, respectively, may be altered. In some embodiments, the function of these proteins may be altered by modulating the activity of Lrch4, which may result in reducing or increasing the function of these proteins in a cell. It should be understood that modulating the function of signaling proteins, adaptor proteins, or transcription factors may have downstream effects. For example, modulating MyD88 function may in turn modulate the expression of IL-8 by a cell.

Also described herein are methods for modulating cytokine production in a cell by altering the activity of Lrch4 in the cell. In some embodiments, Lrch4 activity may be altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing the Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity. Cytokines that may be modulated by the methods described herein include, but are not limited to: tumor necrosis factor alpha (TNF-α), TNF-β, interferon alpha (IFN-α), IFN-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, or IL-35. In some embodiments, cytokine expression may be modulated such that cellular expression is reduced, while in other embodiments, expression may be increased.

Other methods described herein include methods for modulating MyD88-mediated signaling in a cell by altering the activity of Lrch4 in the cell. In some embodiments, Lrch4 activity may be altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA is SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing the Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity. In some embodiments, MyD88-mediated signaling may be modulated such that it is reduced, while in other embodiments, it may be increased.

In addition, this disclosure provides methods for modulating NF-κB activation in a cell by altering the activity of Lrch4 in the cell. In some embodiments, Lrch4 activity may be altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing the Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity. In some embodiments, NF-κB activation may be modulated such that it is reduced, while in other embodiments, it may be increased.

Described herein are methods for modulating activation of a MAP kinase in a cell by altering the activity of Lrch4 in the cell. In some embodiments, Lrch4 activity may be altered by modulating its expression in a cell. In some embodiments Lrch4 modulation reduces its expression in a cell, while in other embodiments its expression increases. Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 may be overexpressed in a cell by transforming the cell with a vector capable of expressing the Lrch4 protein. Lrch4 activity can also altered by exposing the cell to a Lrch4-specific antibody, or a fragment thereof; an isolated Lrch4 ectodomain, or a fragment thereof; or a small molecule modulator of Lrch4 activity. In some embodiments, activation of a MAP kinase may be modulated such that it is reduced, while in other embodiments, it may be increased.

Also disclosed herein are methods of modulating inflammation in a subject by altering the activity of Lrch4. In some embodiments, Lrch4 activity may be altered by modulating its expression in the subject, or in one or more cells of the subject. In some embodiments Lrch4 modulation reduces its expression in the subject, or in one or more cells of the subject, while in other embodiments its expression increases. Lrch4 expression can be reduced by one or more Lrch4-specific polynucleotides, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased by overexpressing a Lrch4 gene in the subject, or in one or more cells of the subject. In one embodiment, Lrch4 may be overexpressed in a cell by transforming one or more cells of a subject with a vector capable of expressing the Lrch4 protein. Lrch4 activity can also altered by exposing the subject, or one or more cells of the subject, to a Lrch4-specific antibody, or a fragment thereof; an isolated Lrch4 ectodomain, or a fragment thereof; or a small molecule modulator of Lrch4 activity. In some embodiments, inflammation may be modulated such that it is reduced, while in other embodiments, it may be increased. For example, inflammation may be reduced in order to treat an inflammatory disease, such as sepsis, which may be caused by exposure to lipopolysaccharides (LPS), lipooligosaccharide (LOS) or other endotoxin; however, in other instances, such as delivery of a vaccine antigen to a subject, it may desirable to increase the inflammatory response to enhance, magnify, or speed up, the subject's immune response. In this regard, inflammation, or the inflammatory response, in a subject may be altered by modifying the activity of Lrch4 to either increase or reduce levels of cytokines including, but not limited to: tumor necrosis factor alpha (TNF-α), TNF-β, interferon alpha (IFN-α), INF-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, or IL-35; or by increasing or reducing the activity of cellular signaling proteins, adaptor proteins, or transcription factors, such as mitogen-activated protein (MAP) kinases, MyD88, or nuclear factor (NF)-κB, respectively.

Provided herein are methods of treating cancer in a subject by altering the activity of Lrch4. In some embodiments, Lrch4 activity may be altered by modulating its expression in the subject, or in one or more cells of the subject. In some embodiments Lrch4 modulation reduces its expression in the subject, or in one or more cells of the subject, while in other embodiments its expression increases. Lrch4 expression can be reduced by one or more Lrch4-specific polynucleotides, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased by overexpressing a Lrch4 gene in the subject, or in one or more cells of the subject. In one embodiment, Lrch4 may be overexpressed in a cell by transforming one or more cells of a subject with a vector capable of expressing the Lrch4 protein. Lrch4 activity can also altered by exposing the subject, or one or more cells of the subject, to a Lrch4-specific antibody, or a fragment thereof; an isolated Lrch4 ectodomain, or a fragment thereof; or a small molecule modulator of Lrch4 activity. In this regard, a subject in need of cancer treatment may be treated by modifying the activity of Lrch4 to alter the function of MyD88, or a mutated form of MyD88. Lrch4 activity could also be modified to either increase or reduce levels of cytokines including, but not limited to: tumor necrosis factor alpha (TNF-α), TNF-β, interferon alpha (IFN-α), INF-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, or IL-35; or by increasing or reducing the activity of cellular signaling proteins, adaptor proteins, or transcription factors, such as mitogen-activated protein (MAP) kinases or nuclear factor (NF)-κB, respectively. Some cancers that may be treated by the methods described herein include, but are not limited to, cancers of the immune system, B-cell lymphomas, non-Hodgkin lymphoma, leukemias, and T-cell lymphomas.

BRIEF DESCRIPTION OF THE DRAWINGS

FIG. 1(a) is a western blot of cytoplasm, membrane, and nuclear cellular fractions. FIG. 1(b) depicts the subcellular localization of GFP-tagged Lrch4 compared to GFP alone (tGFP); DAPI nuclear staining is also as a reference for the relative location of the nuclei of depicted cells.

DETAILED DESCRIPTION OF ILLUSTRATIVE EMBODIMENTS

Definitions

Figure 1:
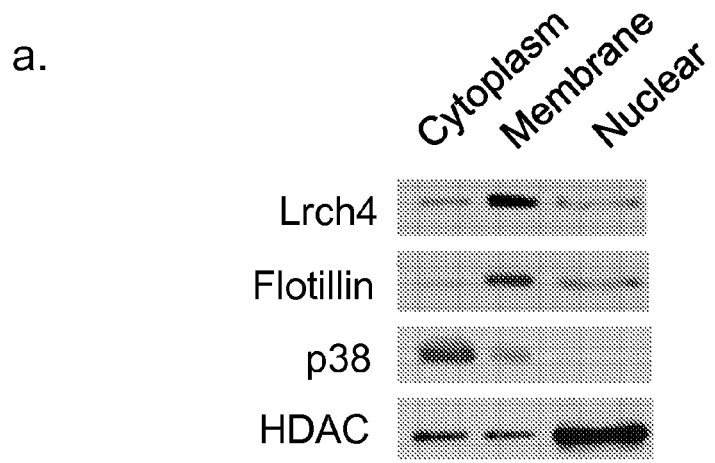
FIG. 1 depicts data that indicates Lrch4 localizes to cellular membranes.
Figure 1:
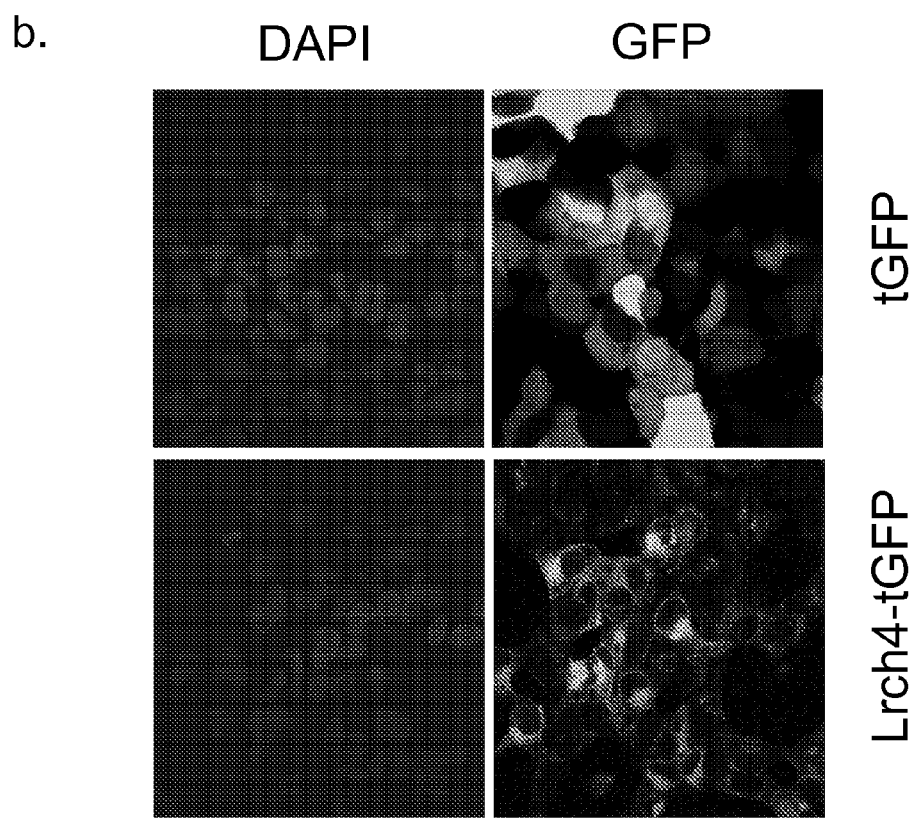

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

An "antibody" as described herein can be of any isotype, including but not limited to IgG, gD, IgA, IgM, IgE, and IgY, and may be derived or obtained from a variety of mammalian sources, such as a bird, mouse, rat, rabbit, monkey, ape, or human. Fragments of an antibody may be any subportion of the entire antibody, such as a variable heavy chain domain, a variable light chain domain, or combinations thereof, a diabody, triabody, tetrabody, bis-scFv, Fab₃, Fab, scFv, or an Fab$_2$ as well as similar such fragments known in the art. The antibody and antibody fragments described herein may mediate the discussed modulating activity by binding to a target antigen, such as Lrch4 and: imparting a structural change to the antigenic protein, causing cellular internalization of the antigenic protein, initiating signaling by the antigenic protein, preventing the antigenic protein from interacting with another protein (for example, preventing dimmer formation or heterologous protein interaction by steric hindrance) or blocking the active site of the antigenic protein.

As used herein, the terms "altering" or "modulating the function of," may mean to change the level of translation, transcription, production of, expression, or activity of a protein or gene to any measurable extent.

As used herein, the terms "altering" or "modulating" the activity of, may mean to change the level of translation, transcription, production, or expression of, or the function of, a protein or gene to any measurable extent.

As used herein, the term "modulating" refers to any measurable change, such as a change in type, kind, or amount.

As used herein, the term "reducing" refers to any measurable decrease.

As used herein, "treatment" shall mean temporary or permanent improvement, alleviation, palliation, remediation or elimination of signs or symptoms of a disease, ailment, or physical malady.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

As used herein, the terms "oligonucleotide" and "polynucleotide" denote polymers of nucleotides. Further, as used herein, the term "target nucleic acid" means a nucleic acid sequence selectively bound by a modulating oligonucleotide and can include polynucleotides having at least a portion of the sense or antisense code for Lrch4. Accordingly, DNA, RNA (including pre-mRNA and mRNA), cDNA, and hybrid nucleic acids such as artificial sequences having at least a portion of the sequence of the Lrch4 coding sequence can be considered a target nucleic acid. Herein, the terms "nucleic acid," "target nucleic acid," and "nucleic acids encoding Lrch4" also include sequences having any of the known base analogs of DNA and RNA such as, but not limited to 4-acetylcytosine, 8-hydroxy-N-6-methyladenosine, aziridinylcytosine, pseudoisocytosine, 5-(carboxyhydroxylmethyl) uracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Sense and antisense oligonucleotides can be chemically modified so as to improve stability in vivo or in vitro. Properties of the polynucleotide can be engineered to impart stability (e.g., nuclease resistance), tighter binding or the desired melting temperature. For example, the polynucleotide can include modified nucleotide analogs, such as those already described. The oligonucleotides contemplated herein can comprise mixtures of naturally occurring nucleotides and nucleotide analogues.

The term "modulatory" oligonucleotide (or polynucleotide) denotes an oligonucleotide having a sequence that enables it to interact with a nucleic acid sequence in such a way that the function of the nucleic acid sequence is altered. The functional alteration that occurs may include, but is not limited to, transcription inhibition, translation inhibition, decreased half-life, transcription upregulation, translation upregulation, and increased half-life. The modulatory oligonucleotides described herein may be either RNA or DNA and have a sequence that is substantially complementary to at least a segment of a selected portion of a nucleic acid sequence. They also encompass, without limitation, antisense molecules, ribozymes, sense molecules and triplex-forming molecules. Modulatory oligonucleotides may disrupt the function of the nucleic acid by specifically hybridizing with it. In some embodiments, however, modulatory oligonucleotides may enhance the function of the nucleic acid either directly or indirectly, for example, by inhibiting a regulatory protein so that translation of a desired protein is upregulated. Some such modulatory oligonucleotides may specifically hybridize to the selected portion of the nucleic acid. Additionally, the modulatory oligonucleotide may have a sequence that is substantially identical to that of the selected portion of the nucleic acid. In some embodiments provided herein modulatory polynucleotides are described as inhibitory polynucleotides, such as inhibitory RNA.

The term "complementary," as used herein, refers to the capacity of two nucleotides to pair with each other. For example, if the nucleotides located at a certain position on two oligonucleotides are capable of hydrogen bonding, then the oligonucleotides are considered to be complementary to each other at that position. The oligonucleotides and the DNA or RNA themselves are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise paring such that stable and specific binding may occur between the oligonucleotides and the DNA or RNA target.

It should be understood that the sequence of a modulating oligonucleotide compound need not be 100 percent complementary to that of its target nucleic acid to be specifically hybridizable. A modulating oligonucleotide compound is specifically hybridizable when binding of the compound to the target DNA or RNA molecule interferes with the normal function of the target DNA or RNA. A sufficient degree of complementarity prevents non-specific binding of the inhibitory oligonucleotide compound to nontarget sequences under conditions in which specific binding is desired, i.e. under physiological conditions in the case of in vivo assays or therapeutic treatment, and in the case of in vitro assays, under conditions in which the assays are performed.

"Identity" refers to the percent of identical sequences between at least two oligonucleotides or polypeptides. The percent identity between the sequences from one moiety to another can be determined by techniques known in the art, for example by direct comparison of aligned sequences. Alternatively, the degree of identity can be determined by hybridization of polynucleotides under conditions which form stable duplexes between identical regions, followed by digestion with single-stranded-specific nuclease(s), and size determination of the digested fragments. Two DNA, or two polypeptide sequences are "substantially identical" to each other when the sequences exhibit at least about 75%-85%, preferably at least about 90%, and most preferably at least about 95%-98% sequence identity over a defined length of the molecules, as determined using the methods above or other such methods known in the art. As used herein, substantially identity also refers to sequences showing complete identity to the specified DNA or polypeptide sequence. DNA sequences that are substantially identical can be identified with Southern hybridization techniques under, for example, stringent conditions, as defined for that particular system. Defining appropriate hybridization conditions in this regard should be within the knowledge of those skilled in the art.

A "subject" as described herein can be any mammal, such as a rodent, rabbit, money, ape, or human.

The term "one or more cells of a subject" includes single cells, functional groups of cells (e.g. a subsegment of a tissue, such as the medulla or cortex of the thymus), or a tissue.

A "functional homologue" or a "functional equivalent" of a given polypeptide includes molecules derived from the wild-type polypeptide sequence, as well as recombinantly-produced or chemically-synthesized polypeptides which function in a manner similar to the wild-type molecule to achieve a desired result. Thus, a functional homologue of Lrch4 encompasses derivatives and analogues of those polypeptides—including any single or multiple amino acid additions, substitutions and/or deletions occurring internally or at the amino or carboxy termini thereof, so long as integration activity remains.

A "vector" is any genetic element, such as a plasmid, phage, transposon, cosmid, chromosome, or a carrier of such an element (e.g., a virus, virion, etc.), which can transfer gene sequences into cells and which may or may not replicate in the host cells or allow for expression of the genetic material encoded by the element. Thus, the term includes cloning and expression vehicles, as well as viral vectors.

"Gene transfer" or "gene delivery" refers to methods or systems for reliably inserting foreign DNA into host cells or organisms. Such methods can result in transient expression of non-integrated transferred DNA, extrachromosomal replication and expression of transferred replicons (e.g., episomes), or integration of transferred genetic material into the genomic DNA of host cells or organisms.

The term "transformation" is used to refer to the uptake of foreign DNA by a cell, and a cell has been "transformed" when exogenous DNA has been introduced inside the cell membrane. Accordingly, the term encompasses transfection and transduction as well as related methods known in the art.

"Knockdown" refers to a cell or organism having reduced expression of one or more genes. As will be appreciated by those skilled in the art, a knockdown will exhibit at least about a 20% reduction in expression, preferably will exhibit at least about a 50% reduction in expression, but can be greater, for example, at least about a 75% reduction in expression. IN addition higher reductions are possible, including at least about a 80%, 81%, 82%, 83%, 84%, 85%, 86%, 87%, 88%, 89%, 90%, 91%, 92%, 93%, 94%, 95%, 96%, 97%, 98%, 99%, or more reduction in expression.

Methods for Modulating TLR-Mediated Signaling

Disclosed herein are methods of modulating TLR-mediated signaling in a cell by altering the activity of Lrch4. In some embodiments Lrch4 activity may be altered to modulate signaling mediated by TLR1, TLR2, TLR3, TLR4, TLR5, TLR6, TLR7, TLR8, TLR9, or TLR10. These embodiments include signaling that is mediated by not only individual and homodimers of the described TLRs, but also of heterodimers of such receptors, such as TLR2/6 or TLR 2/1 heterodimers. In some embodiments, Lrch4 activity is altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating TLR-mediated signaling in a cell can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons.

Cellular TLR-mediated signaling can be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis. In some embodiments the modulatory oligonucleotides described herein can be used to alter signaling mediated by TLR1, in some embodiments the modulatory oligonucleotides described herein can be used to alter signaling mediated by TLR2, in some embodiments the modulatory oligonucleotides described herein can be used to alter signaling mediated by TLR3, in some embodiments the modulatory oligonucleotides described herein can be used to alter signaling mediated by TLR4, in some embodiments the modulatory oligonucleotides described herein can be used to alter signaling mediated by TLR5, in some embodiments the modulatory oligonucleotides described herein can be used to alter signaling mediated by TLR6, in some embodiments the modulatory oligonucleotides described herein can be used to alter signaling mediated by TLR7, in some embodiments the modulatory oligonucleotides described herein can be used to alter signaling mediated by TLR8, in some embodiments the modulatory oligonucleotides described herein can be used to alter signaling mediated by TLR9, in some embodiments the modulatory oligonucleotides described herein can be used to alter signaling mediated by TLR10. These embodiments include signaling that is mediated by not only individual and homodimers of the described TLRs but also of heterodimers of such receptors, such as TLR2/6 or TLR 2/1 heterodimers.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to disrupt TLR-mediated signaling or MyD88 signaling. Such antibodies or ectodomain segments may be used to treat diseases and physiological states that are shown or proposed to be treatable by modulating Lrch4 activity. Accordingly, in some embodiments the described antibodies or ectodomain segments may be used to modulate signaling mediated by TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity for the methods described herein.

Methods for Modulating the Cellular Response to a TLR Ligand

Disclosed herein are methods of modulating a cellular response to a TLR ligand by altering the activity of Lrch4. In some embodiments Lrch4 activity may be altered to modulate a cellular response mediated by a ligand for TLR1, TLR2, TLR3, TLR4, TLR5, TLR6, TLR7, TLR8, TLR9, or TLR10. These embodiments include a cellular response that is mediated by not only ligands of individual and homodimers of the described TLRs, but also of heterodimers of such receptors, such as TLR2/6 or TLR 2/1 heterodimers. The methods disclosed in this regard may be used to modulate one or more of a variety of cellular responses, individually or in combination, to a TLR ligand. For example, in some embodiments, the cellular response that is modulated is cytokine expression. Cytokines that may be modulated by the methods described herein include, but are not limited to: tumor necrosis factor alpha (TNF-α), TNF-β, interferon alpha (IFN-α), INF-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, or a combination thereof. In some embodiments, cytokine expression may be modulated such that cellular expression is reduced, while in other embodiments, expression may be increased. Furthermore, other cellular responses can be modulated by the methods described herein. For example, the function of cellular signaling proteins, adaptor proteins, or transcription factors, such as MAP kinases, MyD88, or NF-κB, respectively, may be altered. In some embodiments, the function of these proteins may be altered by modulating the activity of Lrch4, which may result in reducing or increasing the function of these proteins in a cell. It should be understood that modulating the function of signaling proteins, adaptor proteins, or transcription factors may have downstream effects. For example, modulating MyD88 function may in turn modulate the expression of IL-8 by a cell.

In some embodiments, Lrch4 activity may be altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating a cellular response to a TLR ligand can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons.

A cellular response to a TLR ligand can be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis, which, in some instances, may be caused by exposure to lipopolysaccharides (LPS), lipooligosaccharide (LOS) or other endotoxin. In some embodiments the modulatory oligonucleotides described herein can be used to alter a cellular response to a TLR1 ligand, in some embodiments the modulatory oligonucleotides described herein can be used to alter a cellular response to a TLR2 ligand, in some embodiments the modulatory oligonucleotides described herein can be used to alter a cellular response to a TLR3 ligand, in some embodiments the modulatory oligonucleotides described herein can be used to alter a cellular response to a TLR4 ligand, in some embodiments the modulatory oligonucleotides described herein can be used to alter a cellular response to a TLR5 ligand, in some embodiments the modulatory oligonucleotides described herein can be used to alter a cellular response to a TLR6 ligand, in some embodiments the modulatory oligonucleotides described herein can be used to alter a cellular response to a TLR7 ligand, in some embodiments the modulatory oligonucleotides described herein can be used to alter a cellular response to a TLR8 ligand, in some embodiments the modulatory oligonucleotides described herein can be used to alter a cellular response to a TLR9 ligand, in some embodiments the modulatory oligonucleotides described herein can be used to alter a cellular response to a TLR10 ligand. These embodiments include cellular responses mediated by not only by ligands to individual and homodimers of the described TLRs but also of ligands to heterodimers of such receptors, such as TLR2/6 or TLR 2/1 ligands.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to modulate a cellular response to a TLR ligand. Such antibodies or ectodomain segments may be used to treat diseases and physiological states that are shown or proposed to be treatable by modulating such responses. Accordingly, in some embodiments the described antibodies or ectodomain segments may be used to inhibit responses initiated by ligands for TLR1, TLR2, TLR3, TLR4, TLR5, TLR6, TLR7, TLR8, TLR9, or TLR10. These embodiments include responses mediated by not only by ligands for individual and homodimers of the described TLRs but also for heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide that is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity and, thus can be useful for modulating a cellular response to a TLR ligand.

Methods for Modulating Cytokine Production

Methods described herein also include those for modulating cytokine production in a cell by altering the activity of Lrch4. In some embodiments Lrch4 activity may be altered to modulate cytokine production controlled or influenced by signaling through TLR1, TLR2, TLR3, TLR4, TLR5, TLR6, TLR7, TLR8, TLR9, or TLR10. These embodiments include cytokine production that is mediated by not only individual and homodimers of the described TLRs but also by heterodimers of such receptors, such as TLR2/6 or TLR 2/1 heterodimers. The methods disclosed in this regard may be used to modulate one or more of a variety of cytokines produced, individually or in combination, through TLR signaling or stimulation of other receptors that, when stimulated, may cause cytokine production, such as CD40. Cytokines that may be modulated by the methods described herein include, but are not limited to: tumor necrosis factor alpha (TNF-α), TNF-β, interferon alpha (IFN-α), INF-β, IFN-ω, IFN-γ, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, or a combination thereof. In some embodiments, cytokine expression may be modulated such that cellular expression is reduced, while in other embodiments, expression may be increased. Furthermore, other cellular responses can be modulated by the methods described herein to alter cytokine production. For example, the function of cellular signaling proteins, adaptor proteins, or transcription factors, such as MAP kinases, MyD88, or NF-κB, respectively, may be altered. In some embodiments, the function of these proteins may be altered by modulating the activity of Lrch4, which may result in reducing or increasing the function of these proteins in a cell. It should be understood that modulating the function of signaling proteins, adaptor proteins, or transcription factors may have downstream effects. For example, modulating MyD88 function may in turn modulate the expression of IL-8 by a cell.

In some embodiments, Lrch4 activity may be altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating cytokine expression can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons.

Cytokine production can also be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA is SEQ ID NO: 1, SEQ ID NO: 2, or SEQ ID NO: 3. Conversely, Lrch4 expression can be increased in a cell by overexpressing a Lrch4 gene in a cell. In one embodiment, Lrch4 overexpression may increase cytokine production by a cell. In some embodiments of the methods described herein, Lrch4 overexpression in a cell may result in increased TNFα expression by that cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis, which, in some instances, may be caused by exposure to lipopolysaccharides (LPS), lipooligosaccharide (LOS) or other endotoxin. In some embodiments the modulatory oligonucleotides described herein can be used to alter production of a cytokine that is produced in response to TLR1-mediated signaling, in some embodiments the modulatory oligonucleotides described herein can be used to alter production of a cytokine that is produced in response to TLR2-mediated signaling, in some embodiments the modulatory oligonucleotides described herein can be used to alter production of a cytokine that is produced in response to TLR3-mediated signaling, in some embodiments the modulatory oligonucleotides described herein can be used to alter production of a cytokine that is produced in response to TLR4-mediated signaling, in some embodiments the modulatory oligonucleotides described herein can be used to alter production of a cytokine that is produced in response to TLR5-mediated signaling, in some embodiments the modulatory oligonucleotides described herein can be used to alter production of a cytokine that is produced in response to TLR6-mediated signaling, in some embodiments the modulatory oligonucleotides described herein can be used to alter production of a cytokine that is produced in response to TLR7-mediated signaling, in some embodiments the modulatory oligonucleotides described herein can be used to alter production of a cytokine that is produced in response to TLR8-mediated signaling, in some embodiments the modulatory oligonucleotides described herein can be used to alter production of a cytokine that is produced in response to TLR9-mediated signaling, in some embodiments the modulatory oligonucleotides described herein can be used to alter production of a cytokine that is produced in response to TLR10-mediated signaling. These embodiments include cytokine production mediated by not only by ligands to individual and homodimers of the described TLRs but also of ligands to heterodimers of such receptors, such as TLR2/6 or TLR 2/1 ligands.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to modulate a cellular response to a TLR ligand. Such antibodies or ectodomain segments may be used to treat diseases and physiological states that are shown or proposed to be treatable by modulating such responses. Accordingly, in some embodiments the described antibodies or ectodomain segments may be used to inhibit responses initiated by ligands for TLR1, TLR2, TLR3, TLR4, TLR5, TLR6, TLR7, TLR8, TLR9, or TLR10. These embodiments include responses mediated by not only by ligands for individual and homodimers of the described TLRs but also for heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide that is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity and, thus can be useful for modulating cytokine production.

Methods of Modulating MyD88-Mediated Signaling

Disclosed herein are methods of modulating MyD88-mediated signaling in a cell by altering the activity of Lrch4. In some embodiments Lrch4 activity may be altered to modulate MyD88 signaling associated with signaling pathways initiated through TLR1, TLR2, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. In some embodiments, Lrch4 activity is altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating MyD88-mediated signaling in a cell can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein function can be desirable for a variety of reasons, such as inhibiting a protein central to disease pathogenesis or blocking the function of an inhibitory protein that would otherwise block a desired pathway, to name just two such reasons.

Cellular MyD88-mediated signaling can be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis, which, in some instances, may be caused by exposure to lipopolysaccharides (LPS), lipooligosaccharide (LOS) or other endotoxin. Given the ability of MyD88 to interact with Lrch4, and because MyD88 is involved in the signaling pathways of almost all TLRs and is known to activate NF-κB, its modulation can be important to treating certain diseases or undesirable physiological states that are caused or sustained by direct or indirect activity of Lrch4. Accordingly, in some embodiments the modulatory oligonucleotides described herein may be used to disrupt MyD88-mediated signaling. In some embodiments the modulatory oligonucleotides described herein can be used to alter MyD88 signaling initiated by TLR1, in some embodiments the modulatory oligonucleotides described herein can be used to alter MyD88 signaling initiated by TLR2, in some embodiments the modulatory oligonucleotides described herein can be used to alter MyD88 signaling initiated by TLR4, in some embodiments the modulatory oligonucleotides described herein can be used to alter MyD88 signaling initiated by TLR5, in some embodiments the modulatory oligonucleotides described herein can be used to alter MyD88 signaling initiated by TLR6, in some embodiments the modulatory oligonucleotides described herein can be used to alter MyD88 signaling initiated by TLR7, in some embodiments the modulatory oligonucleotides described herein can be used to alter MyD88 signaling initiated by TLR8, in some embodiments the modulatory oligonucleotides described herein can be used to alter MyD88 signaling initiated by TLR9, in some embodiments the modulatory oligonucleotides described herein can be used to alter MyD88 signaling initiated by TLR10. These embodiments include signaling that is mediated by not only individual and homodimers of the described TLRs but also of heterodimers of such receptors, such as TLR2/6 or TLR 2/1 heterodimers.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR4, TLR5, TLR6, TLR7, TLR8, TLR9, or TLR10. In some embodiments the described antibodies and ectodomain segments inhibit Lrch4 activity, which in turn may be used to disrupt MyD88 signaling. Such antibodies or ectodomain segments may be used to treat diseases and physiological states that are shown or proposed to be treatable by modulating Lrch4 activity. Accordingly, in some embodiments the described antibodies or ectodomain segments may be used to modulate signaling initiated by TLR1, TLR2, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity for the methods described herein.

Methods of Modulating NF-κB Activation

Disclosed herein are methods of modulating NF-κB activation in a cell by altering the activity of Lrch4. In some embodiments Lrch4 activity may be altered to modulate NF-κB activation associated with signaling pathways initiated through TLR1, TLR2, TLR3, TLR4, TLR5, TLR6, TLR7, TLR8, TLR9, or TLR10. These embodiments include signaling that is mediated by not only individual and homodimers of the described TLRs, but also of heterodimers of such receptors, such as TLR2/6 or TLR 2/1 heterodimers. In some embodiments, Lrch4 activity is altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating NF-κB activation in a cell can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons.

Cellular NF-κB activation can be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis, which, in some instances, may be caused by exposure to lipopolysaccharides (LPS), lipooligosaccharide (LOS) or other endotoxin. In some embodiments the modulatory oligonucleotides described herein can be used to alter NF-κB activation initiated by TLR1, in some embodiments the modulatory oligonucleotides described herein can be used to alter NF-κB activation initiated by TLR2, in some embodiments the modulatory oligonucleotides described herein can be used to alter NF-κB activation initiated by TLR3, in some embodiments the modulatory oligonucleotides described herein can be used to alter NF-κB activation initiated by TLR4, in some embodiments the modulatory oligonucleotides described herein can be used to alter NF-κB activation initiated by TLR5, in some embodiments the modulatory oligonucleotides described herein can be used to alter NF-κB activation initiated by TLR6, in some embodiments the modulatory oligonucleotides described herein can be used to alter NF-κB activation initiated by TLR7, in some embodiments the modulatory oligonucleotides described herein can be used to alter NF-κB activation initiated by TLR8, in some embodiments the modulatory oligonucleotides described herein can be used to alter NF-κB activation initiated by TLR9, in some embodiments the modulatory oligonucleotides described herein can be used to alter NF-κB activation initiated by TLR10. These embodiments include signaling that is mediated by not only individual and homodimers of the described TLRs but also of heterodimers of such receptors, such as TLR2/6 or TLR 2/1 heterodimers.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to disrupt NF-κB activation. Such antibodies or ectodomain segments may be used to treat diseases and physiological states that are shown or proposed to be treatable by modulating Lrch4 activity. Accordingly, in some embodiments the described antibodies or ectodomain segments may be used to modulate signaling initiated by TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity for the methods described herein.

Methods of Modulating MAP Kinase Activity

Disclosed herein are methods of modulating MAP kinase activation in a cell by altering the activity of Lrch4. In some embodiments Lrch4 activity may be altered to modulate MAP kinase activation associated with signaling pathways initiated through TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. In some embodiments, Lrch4 activity is altered by modulating its expression in a cell. In some embodiments Lrch4 modulation reduces its expression in a cell, while in other embodiments its expression increases. Expression may be modulated to varying degrees. In some aspects it may be desirable to modulate expression to only a moderate degree, while in other embodiments it may be desirable to modulate expression to an extreme degree. Accordingly, the described methods contemplate embodiments where Lrch4 expression is reduced from about 5% to about 99% of normal expression levels. Specifically, Lrch4 expression may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression is increased from about 5% to about 99% of normal expression levels. Specifically, Lrch4 expression may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity for modulating MAP kinase activation in a cell can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons.

Cellular MAP kinase activation can be modulated by altering the expression of Lrch4 by expressing one or more Lrch4-specific polynucleotides in a cell. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a cell by overexpressing a Lrch4 gene in a cell. The gene in question can be a Lrch4 gene expressed by a vector in a cell, or it can be a gene that encodes a transcriptional or translational regulator that, when expressed in a cell, increases cellular production of Lrch4. In one embodiment, Lrch4 may be overexpressed in a cell by transforming the cell with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as sepsis, which, in some instances, may be caused by exposure to lipopolysaccharides (LPS), lipooligosaccharide (LOS) or other endotoxin. In some embodiments the modulatory oligonucleotides described herein can be used to alter MAP kinase activation initiated by TLR1, in some embodiments the modulatory oligonucleotides described herein can be used to alter MAP kinase activation initiated by TLR2, in some embodiments the modulatory oligonucleotides described herein can be used to alter MAP kinase activation initiated by TLR3, in some embodiments the modulatory oligonucleotides described herein can be used to alter MAP kinase activation initiated by TLR4, in some embodiments the modulatory oligonucleotides described herein can be used to alter MAP kinase activation initiated by TLR5, in some embodiments the modulatory oligonucleotides described herein can be used to alter MAP kinase activation initiated by TLR6, in some embodiments the modulatory oligonucleotides described herein can be used to alter MAP kinase activation initiated by TLR7, in some embodiments the modulatory oligonucleotides described herein can be used to alter MAP kinase activation initiated by TLR8, in some embodiments the modulatory oligonucleotides described herein can be used to alter MAP kinase activation initiated by TLR9, in some embodiments the modulatory oligonucleotides described herein can be used to alter MAP kinase activation initiated by TLR10. These embodiments include signaling that is mediated by not only individual and homodimers of the described TLRs but also of heterodimers of such receptors, such as TLR2/6 or TLR 2/1 heterodimers.

Lrch4 activity can also be altered by exposing the cell to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to disrupt MAP kinase activation. Such antibodies or ectodomain segments may be used to treat diseases and physiological states that are shown or proposed to be treatable by modulating Lrch4 activity. Accordingly, in some embodiments the described antibodies or ectodomain segments may be used to modulate signaling initiated by TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein.

Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity for the methods described herein.

Methods of Treatment

TLR signaling influences a wide range of diseases, including, but not limited to, inflammatory diseases, such as sepsis or endotoxin-induced toxic shock syndrome; respiratory diseases, such as acute respiratory distress syndrome, asthma, and chronic obstructive pulmonary disease; autoimmune diseases, such as systemic lupus erythematosus and rheumatoid arthritis; heart disease, cancer, organ transplant rejection, metabolic syndrome, inflammatory bowel syndrome, and atherosclerosis, among others. Given the ability of Lrch4 modulation to alter TLR-mediated signaling and downstream actors in the TLR signal transduction process, this disclosure provides applicable methods of treatment by modulating the activity of Lrch4 in a subject or one or more cells of a subject. In this regard, methods are disclosed providing for a subject to receive a treatment that modulates the activity of Lrch4 to either increase or reduce levels of cytokines including, but not limited to: tumor necrosis factor alpha (TNF-$\alpha$), TNF-$\beta$, interferon alpha (IFN-$\alpha$), IFN-$\beta$, IFN-$\omega$, IFN-$\gamma$, granulocyte colony-stimulating factor (G-CSF), interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, or IL-35; or by increasing or reducing the activity of cellular signaling proteins, adaptor proteins, or transcription factors, such as mitogen-activated protein (MAP) kinases, MyD88, or nuclear factor (NF)-$\kappa$B, respectively. The methods of treatment provided herein may be useful for treating subjects having inflammatory diseases, such as sepsis or endotoxin-induced toxic shock syndrome; respiratory diseases, such as acute respiratory distress syndrome, asthma, and chronic obstructive pulmonary disease; autoimmune diseases, such as systemic lupus erythematosus and rheumatoid arthritis; heart disease, cancer, organ transplant rejection, metabolic syndrome, inflammatory bowel syndrome, and atherosclerosis, among others. In instances, the described treatments may be used to treat a subject having sepsis, which, in some instances, may be caused by exposure to lipopolysaccharides (LPS), lipooligosaccharide (LOS) or other endotoxin. For example, in one embodiment, a subject may be treated for endotoxin-induced sepsis by administering to the subject a therapeutic amount of a Lrch4-specific inhibitory RNA, such as SEQ ID NO: 1, SEQ ID NO: 2, or SEQ ID NO: 3.

The methods of treatment disclosed herein are focused on modulating the activity of Lrch4 in a subject or in one or more cells of a subject. In some embodiments Lrch4 activity may be altered to modulate signaling pathways initiated through TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers. In other embodiments the activity of Lrch4 is modulated to alter the activity of a signaling molecule such as MyD88 or MAP kinase. In another embodiment, Lrch4 activity is altered to modulate the activity of a transcription factor, such as NF-κB. In some embodiments, Lrch4 activity is altered by modulating its expression in a subject or in one or more cells of a subject. In some embodiments Lrch4 modulation reduces its expression in a cell, while in other embodiments its expression increases. For the treatment methods described herein it may be necessary or desirable to modulate Lrch4 expression or activity to varying degrees. In some aspects it may be desirable to modulate Lrch4 expression or activity to only a moderate degree, while in other embodiments it may be desirable to modulate Lrch4 expression or activity to an extreme degree. Accordingly, the described methods contemplate embodiments where Lrch4 expression or activity is reduced from about 5% to about 99% of normal levels. Specifically, Lrch4 expression or activity may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%. In addition, the described methods also contemplate embodiments where Lrch4 expression or activity is increased from about 5% to about 99% of normal levels. Specifically, Lrch4 expression or activity may be increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, where the term about indicates plus or minus 3%.

Altering Lrch4 protein activity to treat a disease or illness in a subject can be accomplished in many ways. In some instances this can be done before the protein is even formed, by modulating Lrch4 DNA replication or transcription, RNA translocation to the site of translation, RNA translation, RNA splicing, and catalytic activity conducted or aided by RNA. In addition, the activity of the protein itself can be disrupted by direct contact with another protein (e.g., an antibody or, in the context of a receptor, a ligand, or an obstructing peptide, etc.). Disruption of protein activity can be desirable for a variety of reasons, such as inhibiting a protein central to disease pathogenesis or blocking the function of an inhibitory protein that would otherwise block a desired pathway, to name just two such reasons. Lrch4 activity can also be enhanced according to methods provided herein by causing increased expression of the protein in a subject or in one or more cells of a subject.

Lrch4 activity may be modulated to treat a subject in need of such treatment by altering the expression of Lrch4 by expressing one or more Lrch4-specific polynucleotides in a subject or in one or more cells of a subject. The modulatory Lrch4-specific oligonucleotides described herein can be homologous or identical to any portion of the Lrch4 DNA or RNA sequence. In some embodiments, Lrch4 expression can be reduced by one or more Lrch4-specific polynucleotides in a cell, such as an inhibitory RNA, for example, a shRNA or a siRNA. In some embodiments, a Lrch4-specific inhibitory RNA comprises SEQ ID NO: 1, SEQ ID NO: 2, or SEQ ID NO: 3. Conversely, Lrch4 expression can be increased in a subject, or one or more cells of a subject, by overexpressing a Lrch4 gene. The gene in question can be a Lrch4 gene expressed by a vector in a cell, or it can be a gene that encodes a transcriptional or translational regulator that, when expressed in a subject, or one or more cells of a subject, increases cellular production of Lrch4. In one embodiment, Lrch4 may be overexpressed in a subject, or one or more cells of a subject, by transforming one or more cells with an expression vector capable of expressing Lrch4 protein. The Lrch4 gene expressed on a vector can be an isolated form of the native Lrch4 gene, an isolated form of Lrch4 cDNA, or a recombinant Lrch4 gene. The modulatory oligonucleotides described herein can be used to alter the expression of Lrch4 in vitro and in vivo. Accordingly, they may be used in the treatment of certain diseases or undesirable physiological states that are caused or sustained by the direct or indirect activity of Lrch4. For example, Lrch4 expression could be altered to treat one or more TLR-mediated diseases or physiological states, such as inflammatory diseases; respiratory diseases, such as acute respiratory distress syndrome, asthma, and chronic obstructive pulmonary disease; autoimmune diseases, such as systemic lupus erythematosus and rheumatoid arthritis; heart disease, cancer, organ transplant rejection, metabolic syndrome, inflammatory bowel syndrome, and atherosclerosis, among others. In some embodiments the modulatory oligonucleotides described herein can be used to alter MAP kinase activation initiated by TLR1, in some embodiments the modulatory oligonucleotides described herein can be used to alter MAP kinase activation initiated by TLR2, in some embodiments the modulatory oligonucleotides described herein can be used to alter MAP kinase activation initiated by TLR3, in some embodiments the modulatory oligonucleotides described herein can be used to alter MAP kinase activation initiated by TLR4, in some embodiments the modulatory oligonucleotides described herein can be used to alter MAP kinase activation initiated by TLR5, in some embodiments the modulatory oligonucleotides described herein can be used to alter MAP kinase activation initiated by TLR6, in some embodiments the modulatory oligonucleotides described herein can be used to alter MAP kinase activation initiated by TLR7, in some embodiments the modulatory oligonucleotides described herein can be used to alter MAP kinase activation initiated by TLR8, in some embodiments the modulatory oligonucleotides described herein can be used to alter MAP kinase activation initiated by TLR9, in some embodiments the modulatory oligonucleotides described herein can be used to alter MAP kinase activation initiated by TLR10. These embodiments include signaling that is mediated by not only individual and homodimers of the described TLRs but also of heterodimers of such receptors, such as TLR2/6 or TLR 2/1 heterodimers.

Treatment may also be carried out to modulate Lrch4 activity by exposing the subject or one or more cells of a subject to a Lrch4-specific antibody, or a fragment thereof; an isolated Lrch4 ectodomain, or a fragment thereof; or a small molecule modulator of Lrch4 activity. Provided herein are Lrch4-specific antibodies and ectodomain segments that may be used to disrupt or prevent Lrch4 activity by interacting with Lrch4 itself, TLR1, TLR2, TLR3, TLR4, TLR5, TLR6, TLR7, TLR8, TLR9, or TLR10. In some embodiments the described antibodies and ectodomain segments inhibit Lrch4 activity, which in turn may be used to disrupt MAP kinase activation, NF-κB activation, TLR-mediated signaling, or cytokine production, as needed to treat a disease condition or undesirable physiological state. Such antibodies or ectodomain segments may be used to treat diseases and physiological states that are shown or proposed to be treatable by modulating Lrch4 activity. Accordingly, in some embodiments the described antibodies or ectodomain segments may be used to modulate signaling initiated by TLR1, TLR2, TLR3, TLR4, TLR5, TLR6, TLR7, TLR8, TLR9, or TLR10. These embodiments include signaling that is mediated by not only individual and homodimers of the described TLRs but also of heterodimers of such receptors, such as TLR2/6 or TLR 2/1 heterodimers.

It should be understood that Lrch4 peptides, protein segments, Lrch4 itself, and oligonucleotides encoding such peptides, protein segments, or Lrch4, could be used to develop an antibody or ectodomain segment useful for the purposes described herein. In one embodiment the Lrch4-specific antibodies may be specific for a Lrch4 immunogenic peptide is at least about 80% identical to a portion of the Lrch4 protein. More specifically, the Lrch4-derived immunogenic peptide can be about 80, 81, 82, 83, 84, 85, 86, 87, 88, 89, 90, 91, 92, 93, 94, 95, 96, 97, 98, or 99 percent identical to the a portion of the Lrch4 protein. Furthermore, Lrch4 ectodomain peptides or amino acid sequences that are either identical to, or homologous with, the Lrch4 ectodomain can serve as modulators of Lrch4 activity. In one embodiment a Lrch4 ectodomain segment may be specific for a Lrch4 immunogenic peptide that is at least about 80% identical to a portion of the Lrch4 ectodomain. More specifically, the Lrch4-derived ectodomain segment can be about 80, 81, 82, 83, 84, 85, 86, 87, 88, 89, 90, 91, 92, 93, 94, 95, 96, 97, 98, or 99 percent identical to the a portion of the Lrch4 protein ectodomain. In addition, small molecules capable of interacting with Lrch4, either extracellularly or intracellularly, may serve as modulators of Lrch4 activity for the methods described herein. The described Lrch4-specific antibodies, or a fragment thereof; ectodomains, or a fragment thereof; or a small molecule modulators described herein may be administered to a subject, via conventional means known in the art, to treat the subject as needed.

The modulatory oligonucleotides; ectodomain peptides, and fragments thereof; antibodies, and fragments thereof; and small molecule modulators described herein may be incorporated into pharmaceutical compositions. The modulatory oligonucleotides; ectodomain peptides, and fragments thereof; antibodies, and fragments thereof; and small molecule modulators described herein may be used in methods to modulate the expression, function, or activity of Lrch4 in a cell, tissue, or subject. Such methods may use the modulatory oligonucleotides; ectodomain peptides, and fragments thereof; antibodies, and fragments thereof; and small molecule modulators described herein alone, or they may use the pharmaceutical compositions thereof. For example, the described methods of treatment may be carried out using modulatory oligonucleotides; ectodomain peptides, and fragments thereof; antibodies, and fragments thereof; and small molecule modulators incorporated into pharmaceutical compositions with pharmaceutically acceptable carriers such as, for example, xanthan gum, locust bean gum, galactose, other saccharides, oligosaccharides and/or polysaccharides, starch, starch fragments, dextrins, British gum and mixtures thereof. This disclosure encompasses the use of any pharmaceutically acceptable salts, esters, salts of such esters, or any other compounds which, upon administration to an organism such as a human, are capable of providing (directly or indirectly) the biologically active modulatory oligonucleotides, immunogenic peptides, or antibodies described herein to carry out the described methods. Accordingly, for example, the disclosure is also drawn to prodrugs, and other bioequivalents. The compounds described herein may also be admixed, encapsulated, conjugated or otherwise associated with other molecules, molecule structures or mixtures of compounds, as for example, liposomes, receptor targeted molecules, oral, topical and other formulations, for assisting in uptake, distribution and/or absorption.

The pharmaceutical compositions described herein may be administered in a number of ways depending upon whether local or systemic treatment is desired and upon the area to be treated. Administration may be topical (including ophthalmic and to mucous membranes), pulmonary, e.g., by inhalation or insufflation of powders or aerosols, including by nebulizers; and tracheal, intranasal, epidermal, transdermal, oral, or parenteral. Parenteral administration includes intravenous, intraarterial, subcutaneous, intraperitoneal, or intramuscular injection or infusion, as well as intracranial (e.g., intrathecal or intraventricular) administration. Oligonucleotides with at least one 2'-O-methoxyethyl modification are believed to be particularly useful for oral administration. Additionally, the modulatory oligonucleotides described herein may be administered to a subject, such as a mammal, in such a way to allow for cellular expression of the oligonucleotides in the host. For example, the modulatory oligonucleotides may be inserted into an expression vector that is deliverable to specific host cells, inserted in a viral vector that can infect host cells, or delivered via a gene gun apparatus or functional equivalent thereof.

Pharmaceutical compositions and formulations for topical administration may include transdermal patches, ointments, lotions, creams, gels, drops, suppositories, sprays, liquids, and powders. Conventional pharmaceutical carriers, aqueous bases, powder bases or oil bases, thickeners and the like may be necessary or desirable. Topical formulations include those in which the oligonucleotides of the invention are in admixture with a topical delivery agent such as lipids, liposomes, fatty acids, fatty acid esters, steroids, chelating agents and surfactants. Preferred lipids and liposomes may be neutral, negative, and cationic. Oligonucleotides of the invention may be encapsulated within liposomes or may form complexes thereto, such as cationic liposomes. Alternatively, oligonucleotides may be complexed to lipids, including cationic lipids.

The specificity and sensitivity of modulatory oligonucleotides technology can be employed as therapeutic moieties in the treatment of disease or physiologic states in mammals and man. Other drugs, including ribozymes, have been safely and effectively administered to humans, and numerous clinical trials are presently underway. As useful therapeutic modalities, modulatory oligonucleotides, antisense or otherwise, can be configured to be useful in treatment regimes for treatment of cells, tissues, and animals, especially humans.

Disclosed herein are also kits containing the modulatory oligonucleotides; ectodomain peptides, and fragments thereof; antibodies, and fragments thereof; and small molecule modulators described herein. Such kits can contain the described modulatory oligonucleotides alone, placed into a vector, or in combination with a pharmaceutically acceptable carrier, salt, or the like. Similarly the described kits may contain one or more of the described ectodomain peptides, and fragments thereof; antibodies, and fragments thereof; and small molecule modulators either alone or in combination with a pharmaceutically acceptable carrier, salt, or the like. The described kits can also include instructions for using or administering the modulatory oligonucleotides; ectodomain peptides, and fragments thereof; antibodies, and fragments thereof; and small molecule modulators described herein to a subject.

Cells contemplated in the embodiments described in this application can be any cell that expresses Lrch4, MyD88, or a TLR. These cells include, but are not limited to, immune cells, such as B-cells, T-cells, macrophage and other granulocytes. Additional cells contemplated include cancer cells, in some particular embodiments cancer cells associated with cancers of the immune system are contemplated, such as cancerous B-cells of: diffuse large B-cell lymphoma (including activated B-cell-like (ABC) subtypes), non-Hodgkin lymphoma, prolymphocytic leukemia (PLL) and hairy cell leukemia (HCL); in addition, cancerous T-cells (T-cell lymphoma) and granulocytes are also contemplated as being with the scope of the cells for use with the methods described herein (see Ngo et al., Nature e-publication, doi:10.1038/nature09671 (2010), which is incorporated herein by reference).

Modulatory Oligonucleotides

Lrch4 activity can be modulated with an isolated, modulatory oligonucleotide. This can be brought about in a number of ways. While not wishing to be limited by any particular theory, it is believed that modulatory oligonucleotides alter the activity of a target nucleic acid, in part, by binding to a particular target sequence. A modulating oligonucleotide can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote modulatory mechanisms of the cells, such as promoting RNA degradation via RNase action, prolonging the target half-life, or upregulating transcription or translation. It may destabilize RNA, such as mRNA or tRNA, to reduce its half-life. The inhibitory oligonucleotide can bind to the major groove of the duplex DNA to form a triple helical or "triplex" structure. Methods of inhibition using inhibitory polynucleotides therefore encompass a number of different approaches to altering expression of specific genes that operate by different mechanisms. These different types of inhibitory polynucleotide technology are described in C. Helene and J. Toulme, (1990) *Biochim. Biophys. Acta.*, 1049:99-125.

The modulatory oligonucleotides described herein may interfere with the function or activity of Lrch4 mRNA, thus preventing proper protein expression. This interference is commonly referred to as "knockdown" of the target nucleic acid. This may result in the amelioration or reduction of disease symptoms or undesirable physiological state or response attributable, in whole or in part, to Lrch4 activity. One such example is a toll-like receptor-associated inflammatory response. As described herein, "modulation" can mean either an increase or a decrease in the expression of a gene; however, inhibition is typically the form of modulation disclosed.

In some preferred embodiments, genes encoding Lrch4 can be modulated through the use of a variety of other post-transcriptional gene silencing (RNA silencing) techniques. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner.

RNA interference (RNAi) is a mechanism of post-transcriptional gene silencing mediated by double-stranded RNA (dsRNA), which is distinct from antisense and ribozyme-based approaches (see Jain K K Pharmacogenomics (2004) 5:239-42, for a review of RNAi and siRNA). RNA interference is useful in a method for reducing the expression of Lrch4 in an animal such as a human by administering to the animal a nucleic acid (e.g., dsRNA) that specifically hybridizes to a gene encoding Lrch4, and attenuates its expression. RNA interference provides shRNA or siRNA that comprise multiple sequences that target one or more regions of the Lrch4 target gene. DsRNA molecules (shRNA or siRNA) are believed to direct sequence-specific degradation of mRNA in cells of various types after first undergoing processing by an RNase III-like enzyme called DICER (Bernstein E et al. (2001) Nature 409:363-366) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. An siRNA may comprise two RNA strands hybridized together, or may alternatively comprise a single RNA strand that includes a self-hybridizing portion. SiRNAs may include one or more free strand ends, which may include phosphate and/or hydroxyl groups. SiRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In certain embodiments of the invention in which perfect complementarity is not achieved, it is generally preferred that any mismatches be located at or near the siRNA termini.

SiRNAs have been shown to downregulate gene expression when transferred into mammalian cells by such methods as transfection, electroporation, cationic liposome-mediated transfection, or microinjection, or when expressed in cells via any of a variety of plasmid-based approaches. RNA interference using siRNA is reviewed in, e.g., Tuschl T (2002) Nat. Biotechnol. 20:446-8; Yu J-Y et al. (2002) Proc. Natl. Acad. Sci. 99:6047-52; Sui G et al. (2002) Proc. Natl. Acad. Sci. USA., 99:5515-20; Paddison P J et al. (2002) Genes and Dev. 16:948-58; Brummelkamp T R et al. (2002) Science 296:550-3, 2002; Miyagashi M et al. (2002) Nat. Biotech. 20:497-500; and, Paul C P et al. (2002) *Nat. Biotechnol.* 20:505-8. As described in these and other references, the siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is preferred to target exons rather than introns, and it may also be preferable to select sequences complementary to regions within the 3' portion of the target transcript. Generally it is preferred to select sequences that contain approximately equimolar ratio of the different nucleotides and to avoid stretches in which a single residue is repeated multiple times.

SiRNAs may thus comprise RNA molecules having a double-stranded region approximately 19 nucleotides in length with 1-2 nucleotide 3' overhangs on each strand, resulting in a total length of between approximately 21 and 23 nucleotides. As used herein, siRNAs also include various RNA structures that may be processed in vivo to generate such molecules. Such structures include RNA strands containing two complementary elements that hybridize to one another to form a stem, a loop, and optionally an overhang, such as a 3' overhang. In some embodiments, the stem is approximately 19 by long, the loop is about 1-20 nt long, although some embodiments will use loops of about 4-10 or about 6-8 nt and/or the overhang is about 1-20, but in some embodiments can be about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs, as described above, trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop (Grishok A et al. (2001) Cell 106:23-4; Hutvagner G et al. (2001) Science 293:834-8; Ketting R F et al. (2001) Genes Dev. 15:2654-9). Endogenous RNAs of this type have been identified in a number of organisms including mammals, suggesting that this mechanism of post-transcriptional gene silencing may be widespread. MicroRNAs have been shown to block translation of target transcripts containing target sites in mammalian cells (Zeng Y et al. (2002) Mol. Cell 9:1327-33).

SiRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target and the mRNA include nonpaired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (McManus M T et al. (2002) RNA 8:842-50). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus it is evident that a diverse set of RNA molecules containing duplex structures is able to mediate silencing through various mechanisms. For the purposes of this disclosure, any such RNA, one portion of which binds to a target oligonucleotide and reduces its expression, whether by triggering degradation, by inhibiting translation, or by other means, is considered to be an siRNA, and any structure that generates such an siRNA (i.e., serves as a precursor to the RNA, such as shRNA) is useful in the practice of the present invention.

A further method of RNA interference for use in the present invention is the use of short hairpin RNAs (shRNA). A plasmid containing a DNA sequence encoding for a particular desired siRNA sequence is delivered into a target cell via transformation or viral infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of a desired protein. The use of shRNA has an advantage over siRNA transfection as the former can lead to stable, long-term inhibition of protein expression Inhibition of protein expression by transfected siRNAs is a transient phenomenon that does not occur for times periods longer than several days. In some cases, this may be preferable and desired. In cases where longer periods of protein inhibition are necessary, shRNA mediated inhibition is preferable. The use of shRNA is particularly preferred. Typically, siRNA-encoding vectors are constructs comprising a promoter, a sequence of the target gene to be silenced in the "sense" orientation, a spacer, the antisense of the target gene sequence, and a terminator.

Reducing the expression of Lrch4 can also be effectuated by other means that are known and readily practiced in the art. For example, antisense nucleic acids can be used. Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA (Denhardt D T (1992) Ann. N Y Acad. Sci. 660:70-6, 1992; Nellen W et al. (1993) Trends Biochem. Sci. 18:419-23; and, Baker B F et al. (1999) Biochim Biophys. Acta. 1489: 3-18). Accordingly, in certain embodiments, Lrch4 expression in a cell is reduced by expressing an antisense nucleic acid molecule in the cell.

Antisense oligonucleotides are generally single-stranded nucleic acid sequences (DNA, RNA, modified DNA, or modified RNA) complementary to a portion of a target oligonucleotide (e.g., an mRNA transcript) and therefore are able to bind to the target to form a duplex. Typically, they are oligonucleotides that range from about 15 to about 35 nucleotides in length but may range from about 10 up to approximately about 50 nucleotides in length. Binding typically reduces or inhibits the function of the target nucleic acid, such as a gene encoding Lrch4. For example, antisense oligonucleotides may block transcription when bound to genomic DNA, inhibit translation when bound to mRNA, and/or lead to degradation of oligonucleotides. Inhibition of the expression of Lrch4 can be achieved by the administration of antisense nucleic acids or peptide nucleic acids comprising sequences complementary to those of the mRNA that encodes Lrch4. Antisense technology and its applications are well known in the art and are described in Phillips, M. I. (ed.) *Antisense Technology, Methods Enzymol.,* 2000, Volumes 313 and 314, Academic Press, San Diego, and references mentioned therein. See also Crooke, S. (ed.) "ANTISENSE DRUG TECHNOLOGY: PRINCIPLES, STRATEGIES, AND APPLICATIONS" ($1^{st}$ Edition) Marcel Dekker; and references cited therein.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) (Wagner R W (1995) Nat. Medicine 1:1116-8; Varga L V et al. (1999) Immun. Lett. 69:217-24; Neilsen P E (1999) Curr. Opin. Biotech. 10:71-5; and, Woolf T M (1990) Nucleic Acids Res. 18:1763-9).

Reduction of Lrch4 expression can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation (Cotten M et al. (1989) EMBO J. 8: 3861-6, 1989; and, Usman N et al. (1996) Curr. Opin. Struct. Biol. 1:527-33).

In some embodiments of the described methods, the cells used can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art, including those described and exemplified herein. In some embodiments, the inhibitory nucleic acid molecules comprise SEQ ID NO: 1 or 2 or analogs, homologs, derivatives, or allelic variants thereof. In some embodiments, Lrch4 modulatory oligonucleotides can have a sequence that is at least about 70% identical to that of SEQ ID NO: 1 or 2. That is to say that an oligonucleotide with about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to either SEQ ID NO: 1 or 2, in a sense or antisense orientation may have an inhibitory effect on Lrch4 expression and be useful for the purposes described herein.

Lrch4-Specific Antibodies

Recombinant antibodies, and fragments thereof, for modulating Lrch4 activity are provided according to the present invention using known techniques based on the teaching provided herein. See, e.g., Ausubel et al., eds. *Current Protocols in Molecular Biology,* Wiley Interscience, N.Y. (1987, 1992, 1993); and Sambrook et al. *Molecular Cloning: A Laboratory Manual,* Cold Spring Harbor Laboratory Press (1989), the entire contents of which are incorporated herein by reference.

The DNA encoding a Lrch4-specific antibody of the present invention can be genomic DNA or cDNA which encodes at least one of the heavy chain constant region ($C_H$), the heavy chain variable region ($V_H$), the light chain variable region ($V_L$) and the light chain constant regions ($C_L$). A convenient alternative to the use of chromosomal gene fragments as the source of DNA encoding the murine V region antigen-binding segment is the use of cDNA for the construction of chimeric immunoglobulin genes, e.g., as reported by Liu et al., *Proc. Natl. Acad. Sci., USA* 84:3439 (1987) and *J. Immunology* 139: 3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

Such techniques for synthesizing such oligonucleotides are well known and disclosed by, for example, Wu, et al., *Prog. Nucl. Acid. Res. Molec. Biol.* 21:101-141 (1978), and Ausubel et al., eds. *Current Protocols in Molecular Biology,* Wiley Interscience (1987, 1993), the entire contents of which are herein incorporated by reference.

Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual Lrch4-specific antibody encoding sequence can be estimated by considering abnormal base pairing relationships and the frequency with which a particular codon is actually used (to encode a particular amino acid) in eukaryotic or prokaryotic cells expressing a Lrch4-specific antibody or fragment. Such "codon usage rules" are disclosed by Lathe, et al., *J. Molec. Biol.* 183:1-12 (1985). Using the "codon usage rules" of Lathe, a single oligonucleotide, or a set of oligonucleotides, that contains a theoretical "most probable" nucleotide sequence capable of encoding a Lrch4-specific variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding a Lrch4-specific antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region of a Lrch4-specific antibody gene (Sambrook et al., infra).

A suitable oligonucleotide, or set of oligonucleotides, which is capable of encoding a fragment of the variable or constant region of a Lrch4-specific antibody (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing Lrch4-specific antibodies or variable or constant regions thereof. Single stranded oligonucleotide molecules complementary to the "most probable" variable or Lrch4-specific antibody constant region peptide coding sequences can be synthesized using procedures which are well known to those of ordinary skill in the art (Belagaje, et al., *J. Biol. Chem.* 254: 5765-5780 (1979); Maniatis, et al., In: Molecular Mechanisms in the Control of Gene Expression, Nierlich, et al., Eds., Acad. Press, NY (1976); Wu, et al., *Prog. Nucl. Acid Res. Molec. Biol.* 21: 101-141 (1978); Khorana, *Science* 203: 614-625 (1979)). Additionally, DNA synthesis can be achieved through the use of automated synthesizers. Techniques of nucleic acid hybridization are disclosed by Sambrook et al. (infra), and by Hayrnes, et al. (In: Nucleic Acid Hybridization, A Practical Approach, IRL Press, Washington, D.C. (1985)), which references are herein incorporated by reference. Techniques such as, or similar to, those described above have successfully enabled the cloning of genes for human aldehyde dehydrogenases (Hsu, et al., *Proc. Natl. Acad. Sci. USA* 82: 3771-3775 (1985)), fibronectin (Suzuki, et al., *Bur. Mol. Biol. Organ. J.* 4: 2519-2524 (1985)), the human estrogen receptor gene (Walter, et al., *Proc. Natl. Acad. Sci. USA* 82: 7889-7893 (1985)), tissue-type plasminogen activator (Pennica, et al., *Nature* 301: 214-221 (1983)) and human term placental alkaline phosphatase complementary DNA (Keun, et al., *Proc. Natl. Acad. Sci. USA* 82: 8715-8719 (1985)).

In an alternative way of cloning a polynucleotide encoding a Lrch4-specific variable or constant region, a library of expression vectors is prepared by cloning DNA or, more preferably, cDNA (from a cell capable of expressing a Lrch4-specific antibody or variable or constant region) into an expression vector. The library is then screened for members capable of expressing a protein which competitively inhibits the binding of a Lrch4-specific antibody and which has a nucleotide sequence that is capable of encoding polypeptides that have the same amino acid sequence as Lrch4-specific antibodies or fragments thereof. In this embodiment, DNA, or more preferably cDNA, is extracted and purified from a cell which is capable of expressing a Lrch4-specific antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11: 591-595 (Can 1993); Marks et al., *Bio/Technology* 11: 1145-1149, 1993. Once nucleic acid encoding such variable or constant regions is isolated, the nucleic acid can be appropriately expressed in a host cell, along with other constant or variable heavy or light chain encoding nucleic acid, in order to provide recombinant mAbs that bind Lrch4 with inhibitory activity. Such antibodies include a murine or human variable region which contains a framework residue having complimentarity determining residues which are responsible for antigen binding.

Genes encoding the constant (C) regions of the murine and chimeric antibodies, fragments and regions of the described antibodies can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ, or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or mu (IgM).

Human Antibodies and Humanization of Antibodies

Human antibodies avoid certain problems associated with antibodies that possess murine or rat variable and/or constant regions. The presence of such murine or rat derived proteins can lead to the rapid clearance of the antibodies or can lead to the generation of an immune response against the antibody by a subject. In order to avoid the utilization of murine or rat derived antibodies, it has been postulated that one can develop humanized antibodies or generate fully human antibodies through the introduction of human antibody function into a rodent so that the rodent would produce antibodies having fully human sequences.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs) an important milestone towards fulfilling the promise of antibody therapy in human disease. Fully human antibodies are expected to minimize the immunogenic and allergic responses intrinsic to mouse or mouse-derivatized mAbs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al., *Nature Genetics* 7: 13-21, 1994. The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al., *Nature Genetics* 15: 146-156, 1997, Green and Jakobovits, *J. Exp. Med.* 188: 483-495, 1998, and U.S. patent application Ser. No. 08/759,620, filed Dec. 3, 1996, the disclosures of which are hereby incorporated by reference.

A transgenic mouse possessing an Ig locus has been produced through use of the minilocus approach. An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against Lrch4 in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris, *Immunol Today* 14: 43-46, 1993 and Wright et al., *Crit. Reviews in Immunol.* 12:125-168, 1992. The antibody of interest may be engineered by recombinant DNA techniques to substitute the $C_H1$, $C_H2$, $C_H3$, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., *PNAS USA* 84: 3439, 1987 and *J. Immunol.* 139: 3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, NIH publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG2, IgG3 and IgG4. Particularly preferred isotypes for antibodies of the invention are IgG2 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human $C_H$ or $C_L$ immunoglobulin sequence, with appropriate restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al., *Mol. Cell. Bio.* 3: 280, 1983), Rous sarcoma virus LTR (Gorman et al., *P.N.A.S.* 79: 6777, 1982), and moloney murine leukemia virus LTR (Grosschedl et al., *Cell* 41: 885, 1985); native 1 g promoters, etc.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau, *PNAS USA* 94: 4937-4942, 1997 (ribosomal display), Parmley and Smith, *Gene* 73: 305-318, 1988 (phage display), Scott, *TIBS* 17: 241-245, 1992, Cwirla et al., *PNAS USA* 87: 6378-6382, 1990, Russel et al., *Nucl. Acids Research* 21: 1081-1085, 1993, Hoganboom et al., *Immunol. Reviews* 130: 43-68, 1992, Chiswell and McCafferty, *TIBTECH* 10: 80-84, 1992, and U.S. Pat. No. 5,733,743. If display technologies are utilized to produce antibodies that are not human, such antibodies can be humanized as described above.

Using these techniques, antibodies specific to Lrch4 can be generated. Such antibodies, or fragments thereof may be directed to Lrch4 epitopes or peptides and expression libraries thereof (see e.g. U.S. Pat. No. 5,703,057) which can thereafter be screened as described above for the activities described above.

Design and Generation of Other Therapeutics

In accordance with the present invention and based on the activity of the antibodies that are produced and described herein with respect to Lrch4, the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunotoxins, and radiolabeled therapeutics, generation of peptide therapeutics, gene therapies, particularly intrabodies, antisense therapeutics, and small molecules. Furthermore, as discussed above, the effector function of the antibodies of the invention may be changed by isotype switching to an IgG1, IgG2, IgG3, IgG4, IgD, IgA, IgE, or IgM for various therapeutic uses.

In connection with the generation of advanced antibody therapeutics, where complement fixation is a desirable attribute, it may be possible to sidestep the dependence on complement for cell killing through the use of bispecifics, immunotoxins, or radiolabels, for example.

In connection with bispecific antibodies, bispecific antibodies can be generated that comprise (i) two antibodies one with a specificity to Lrch4 and another to a second molecule that are conjugated together, (ii) a single antibody that has one chain specific to Lrch4 and a second chain specific to a second molecule, or (iii) a single chain antibody that has specificity to Lrch4 and the other molecule. Such bispecific antibodies can be generated using techniques that are well known for example, in connection with (i) and (ii) see e.g., Fanger et al., *Immunol Methods* 4: 72-81, 1994 and Wright and Harris, supra. and in connection with (iii) see e.g., Traunecker et al., *Int. J. Cancer* 7: 51-52, 1992.

In addition, "Kappabodies" (Ill et al., *Protein Eng* 10: 949-57, 1997), "Minibodies" (Martin et al., *EMBO J.* 13: 5303-9, 1994), "Diabodies" (Holliger et al., *PNAS USA* 90: 6444-6448, 1993), or "Janusins" (Traunecker et al., *EMBO J* 10: 3655-3659, 1991) and Traunecker et al., *Int J Cancer* 7:51-52, 1992) may also be prepared.

In connection with immunotoxins, antibodies can be modified to act as immunotoxins utilizing techniques that are well known in the art. See e.g., Vitetta, *Immunol Today* 14: 252, 1993. See also U.S. Pat. No. 5,194,594. In connection with the preparation of radiolabeled antibodies, such modified antibodies can also be readily prepared utilizing techniques that are well known in the art. See e.g., Junghans et al., Cancer Chemotherapy and Biotherapy 655-686 (2d edition, Chafier and Longo, eds., Lippincott Raven, 1996). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing Lrch4, and particularly those cells in which the antibodies of the invention are effective.

In connection with the generation of therapeutic peptides, through the utilization of structural information related to Lrch4 and antibodies thereto, such as the antibodies of the invention (as discussed herein in connection with small molecules) or screening of peptide libraries, therapeutic peptides can be generated that are directed against Lrch4. Design and screening of peptide therapeutics is discussed in connection with Houghten et al., *Biotechniques* 13: 412-421, 1992, Houghten *PNAS USA* 82: 5131-5135, 1985, Pinalla et al., *Biotechniques* 13: 901-905, 1992, Blake and Litzi-Davis, *BioConjugate Chem.* 3: 510-513, 1992. Immunotoxins and radiolabeled molecules can also be prepared, and in a similar manner, in connection with peptidic moieties as discussed above in connection with antibodies.

Important information related to the binding of an antibody to an antigen can be gleaned through phage display experimentation. Such experiments are generally accomplished through panning a phage library expressing random peptides for binding with the antibodies of the invention to determine if peptides can be isolated that bind. If successful, certain epitope information can be gleaned from the peptides that bind.

In general, phage libraries expressing random peptides can be purchased from New England Biolabs (7-mer and 12-mer libraries, Ph.D.-7 Peptide 7-mer Library Kit and Ph.D.-12 Peptide 12-mer Library Kit, respectively) based on a bacteriophage M13 system. The 7-mer library represents a diversity of approximately $2.0 \times 10^9$ independent clones, which represents most, if not all, of the $20^7 = 1.28 \times 10^9$ possible 7-mer sequences. The 12-mer library contains approximately $1.9 \times 10^9$ independent clones and represents only a very small sampling of the potential sequence space of $20^{12} = 4.1 \times 10^{15}$ 12-mer sequences. Each of 7-mer and 12-mer libraries are panned or screened in accordance with the manufacturer's recommendations in which plates were coated with an antibody to capture the appropriate antibody (a goat anti-human IgG Fc for an IgG antibody for example) followed by washing. Bound phage are eluted with 0.2 M glycine-HCl, pH 2.2. After 3 rounds of selection/amplification at constant stringency (0.5% Tween), through use of DNA sequencing, one can characterize clones from the libraries that are reactive with one or more of the antibodies. Reactivity of the peptides can be determined by ELISA. For an additional discussion of epitope analysis of peptides see also Scott and Smith, *Science* 249: 386-390, 1990; Cwirla et al., *PNAS USA* 87: 6378-6382, 1990; Felici et al., *J. Mol. Biol.* 222: 301-310, 1991, and Kuwabara et al., *Nature Biotechnology* 15: 74-78, 1997.

The design of gene and/or antisense therapeutics through conventional techniques is also facilitated through the present invention. Such modalities can be utilized for modulating the activity or function of Lrch4. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al., *Human Gene Therapy* 5: 595-601, 1994 and Marasco,

*Gene Therapy* 4: 11-15, 1997. General design of and considerations related to gene therapeutics is also discussed in International Patent Application No. WO 97/38137. Genetic materials encoding an antibody of the invention may be included in a suitable expression system (whether viral, attenuated viral, non-viral, naked, or otherwise) and administered to a host for in vivo generation of the antibody in the host.

Small Molecule Modulators of Lrch4 Activity

Small molecule therapeutics can also be envisioned in accordance with the present invention. Drugs can be designed to modulate the activity of Lrch4 based upon the present invention. Knowledge gleaned from the structure of the Lrch4 molecule and its interactions with other molecules in accordance with the present invention such as Lrch4-specific antibodies other ligands can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of Lrch4. Such structures can be synthesized chemically or expressed in biological systems. This approach has been reviewed in Capsey et al., Genetically Engineered Human Therapeutic Drugs (Stockton Press, NY, 1988). Indeed, the rational design of molecules (either peptides, peptidomimetics, small molecules, or the like) based upon known, or delineated, structure-activity relationships with other molecules (such as antibodies in accordance with the invention) has become generally routine. See, e.g., Fry et al., *Proc Natl Acad Sci USA* 95: 12022-7, 1998; Hoffman et al., *J Mol Biol* 282: 195-208, 1998; Ginalski et al., *Acta Biochim Pol* 44: 557-64, 1997; Jouko et al., *Biochem J* 322: 927-35, 1997; Singh et al., *J Med Chem* 40: 1130-5, 1997; Mandel et al., *Nat Biotechnol* 14: 323-8, 1996; Monfardini et al., *Proc Assoc Am Physicians* 108: 420-31, 1996; Furet et al., *J Comput Aided Mol Des* 9: 465-72, 1995. Further, combinatorial libraries can be designed and synthesized and used in screening programs, such as high throughput screening efforts.

Lrch4 Ectodomain Segments

Described herein are Lrch4 ectodomain segments capable of modulating cellular activity, typically associated with, directly or indirectly, endogenous Lrch4 activity, as described previously. The Lrch4 ectodomain segments described herein can be produced in a variety of ways, such as via an expression library expressing fragments of the full-length Lrch4 ectodomain to identify fragments that, when expressed, modulate Lrch4 activity (or related cellular activity); using binding studies to determine binding sites of interest on the Lrch4 ectodomain that, when bound activate or initiate Lrch4 activity; or determining Lrch4 ligand binding sites, to allow for isolated fragments of these binding sites to be expressed separately and apart from Lrch4 to inhibit interaction between endogenous Lrch4 and its ligands.

The Lrch4 ectodomain segments described herein can be synthesized as DNA, in some embodiments cDNA, molecules that can encode amino acid segments that have the sequence, or a homologous sequence, to a portion of the Lrch4 ectodomain. The homology of such a sequence, can be at least 80% identical to a desired segment of the Lrch4 ectodomain, and in particular may be 80%, 81%, 82%, 83%, 84%, 85%, 86%, 87%, 88%, 89%, 90%, 91%, 92%, 93%, 94%, 95%, 96%, 97%, 98%, or 99% identical to a desired segment of the Lrch4 ectodomain. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems. Techniques for synthesizing such oligonucleotides are well known and disclosed by, for example, Wu, et al., *Prog. Nucl. Acid. Res. Molec. Biol.* 21:101-141 (1978), and Ausubel et al., eds. *Current Protocols in Molecular Biology*, Wiley Interscience (1987, 1993), the entire contents of which are herein incorporated by reference.

The described oligonucleotides capable of encoding a Lrch4 segment amino acid sequence can be expressed in a host cell, such as a bacterial, insect, or mammalian host cell, or other such expression system to produce the Lrch4 ectodomain segment of interest. The ectodomain segment can then be isolated by methods known to those of skill in the art (i.e., affinity, ion-exchange, or size exclusion chromatography, among other methods). In some embodiments, the described Lrch4 ectodomain can be attached to other proteins to either prolong its half-life; add effector functions, such as immunomodulatory functions associated with an antibody constant region; or provide added structural support to ensure that the ectodomain segment assumes a desired structural conformation.

Treatment Regimes

Also described are pharmaceutical compositions comprising one or a combination of antibodies, e.g., antibodies to Lrch4 (monoclonal, polyclonal or single chain Fv; intact or binding fragments thereof), small molecules, or Lrch4 ectodomain segments formulated together with a pharmaceutically acceptable carrier. Some compositions include a combination of multiple (e.g., two or more) monoclonal antibodies or antigen-binding portions thereof, small molecules, or Lrch4 ectodomain segments described herein. In some compositions, each of the antibodies or antigen-binding portions thereof of the composition is a monoclonal antibody or a human sequence antibody that binds to a distinct, pre-selected epitope of an antigen.

In prophylactic applications, pharmaceutical compositions or medicaments are administered to a subject susceptible to, or otherwise at risk of a disease or condition (i.e., a neoplastic disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a subject suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective Dosages

Effective doses of the antibody compositions, small molecules, or Lrch4 ectodomain segments described herein for the treatment of a disease or undesirable physiological condition or state, cancer-related conditions and diseases, and inflammatory conditions described herein vary depending upon many different factors, including means of administration, target site, physiological state of the subject, whether the subject is human or an animal, other medications administered, and whether treatment is prophylactic or therapeutic. Usually, the subject is a human but nonhuman mammals including transgenic mammals can also be treated. Treatment dosages need to be titrated to optimize safety and efficacy.

For administration with an antibody, small molecules, or a Lrch4 ectodomain segment the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration daily, once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the subject. In some methods, dosage is adjusted to achieve a plasma antibody concentration of 1-1000 µg/ml and in some methods 25-300 µg/ml. Alternatively, an antibody, small molecule, or Lrch4 ectodomain segment can be administered as a sustained release formulation, in which case less frequent administration is required. Dosage and frequency vary depending on the half-life of the antibody, small molecule, or Lrch4 ectodomain segment in the subject. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per subject. Doses for infectious viral vectors vary from 10-100, or more, virions per dose.

Formulation

Antibody, small molecule, or Lrch4 ectodomain segment compositions for inducing a modulatory response may be administered as pharmaceutical compositions comprising an active therapeutic agent, i.e., and a variety of other pharmaceutically acceptable components. (See Remington's Pharmaceutical Science, 15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies, small molecules, or Lrch4 ectodomain segments can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., *Nature* 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

The following examples are provided to describe the invention in greater detail. They are intended to illustrate, not to limit, the invention.

Example I

Lrch4 Localizes to the Plasma Membrane of Macrophage

Experiments were performed to determine the cellular localization of Lrch4 in macrophage cells. Murine RAW 264.7 macrophage cells (obtained from the American Type Culture Collection) were cultured in DMEM supplemented with 10% heat-inactivated fetal bovine serum, 100 µg/ml streptomycin, and 100 U/ml penicillin in a humidified 5% $CO_2$ atmosphere at 37° C. Cultured macrophages were collected and fractionated into membrane, cytosolic, and nuclear fractions using the Subcellular Protein Fractionation Kit (Thermo Scientific) per manufacturer's instructions. The subcellular fractions were normalized by protein content (Bradford protein assay), resolved using a 10% gel by SDS-PAGE, transferred to a nitrocellulose membrane, and blocked in 5% milk/TTBS. Proteins were detected using Lrch4-specific rabbit antisera, p38-specific rabbit antisera (Santa Cruz), mouse anti-flotillin-1 antibody (BD Biosciences), and histone deacetylase (HDAC)-specific anti-sera and were imaged by species-specific HRP-conjugated secondary antibodies, followed by standard electrochemoluminescence and exposure to film. As shown in FIG. 1a, Lrch4 is predominantly localized to the membrane fraction of macrophage.

To confirm that Lrch4 preferentially localized to the macrophage membrane, immunoflorescence experiments using a Lrch4-GFP fusion protein (Lrch4-tGFP) were conducted to allow the cellular distribution of Lrch4 to be observed in situ. A pCMV6-AC-GFP expression plasmid for human Lrch4 was obtained from Origene. hMD2-CD14-293 cells cultured on pre-cleaned, sterile glass-cover slips were transfected with 0.5 µg/well of pCMVAC-Lrch4-GFP plasmid per cover slip using Lipofectamine™ 2000 transfection reagent (Invitrogen) according to the manufacturer's instructions. After 48 hours the culture medium was removed from cells on cover slips and 1 ml of 4% p-formaldehyde fixative was added per well. Cells were fixed for 20 minutes at room temperature without agitation to preserve fine structures. The fixative was aspirated and cells washed three times with 1×PBS. Just before mounting, 2 ml of water was added per well to remove salts. Cells were mounted on a small drop of SlowFade® Gold that contains DAPI (Invitrogen), on a clean glass slide. The edges of the cover slip were sealed, covered, and allowed to dry overnight at 4° C. Cells were visualized the next day using a 660× objective of a confocal microscope (Laser-scanning Microscope Zeiss LSM 510 NLO Meta). The results are depicted in FIG. 1b, which shows Lrch4-tGFP localized to cellular membranes rather than intranuclear (DAPI) or the cytoplasm (tGFP).

Example II

Transcript Expression of Lrch1, 2, 3, and 4 in Murine Tissues

Figure 2:
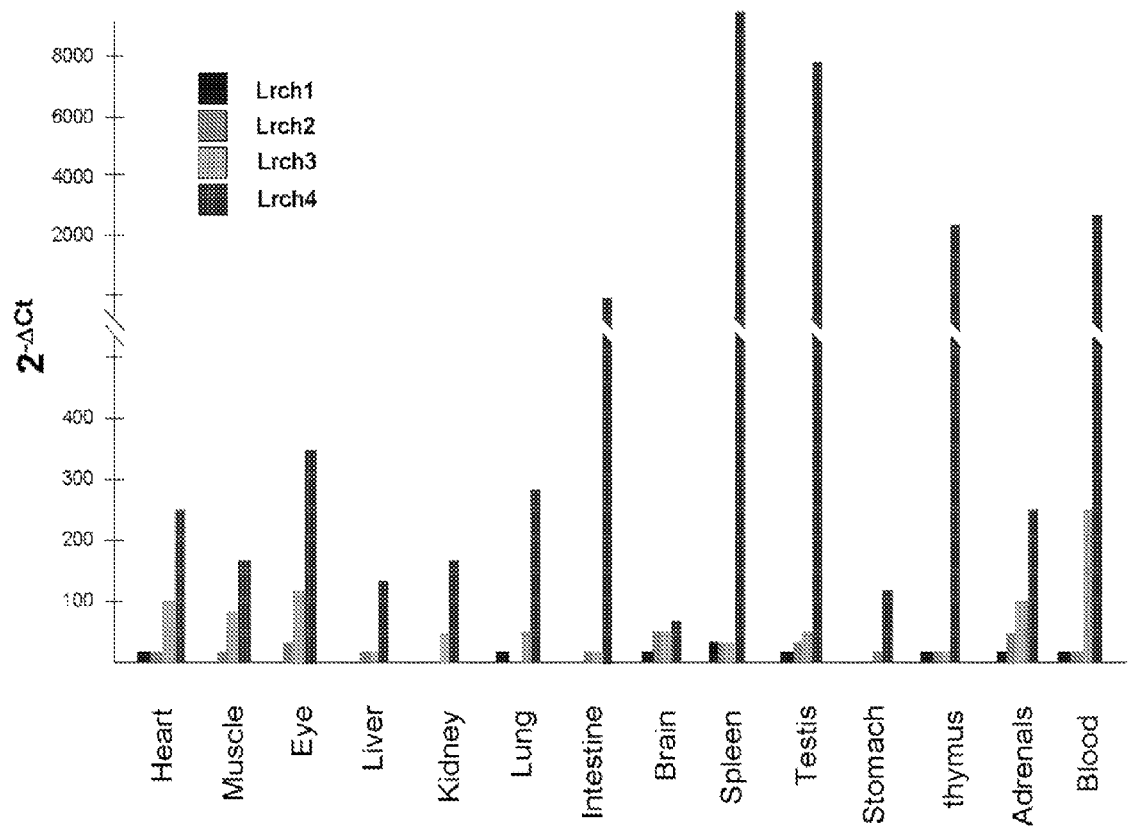
FIG. 2 illustrates the relative expression levels of Lrch1, 2, 3, and 4 in various murine tissues.

To assess the levels of Lrch expression in various tissues, we utilized a SYBR-Green based real-time Reverse Transcriptase PCR. Primer pairs for Lrch1, 2, 3, 4 and GAPDH were custom designed and synthesized (Integrated DNA Technologies Inc. Coralville, Iowa) to be 20 bp in length, have similar Tm values and similar product sizes. Total RNA was extracted from isolated tissues with RNeasy kits (Qiagen) according to the manufacturer's protocol. DNase treatment of the RNA was performed with DNase Set (Qiagen) to remove residual DNA before reverse transcriptase (RT). Reverse Transcription was carried out using random hexamers and the SuperScript First-Strand Synthesis System (based on Invitrogen's protocol). Real-time PCR reactions were performed according to the manufacturer's instructions (PE Applied-Biosystems) in the presence of SYBR-Green reagent. Negative controls, consisted of all components except for RT enzyme. Reactions were run in duplicate on an ABI Prism 7900HT with thermal cycling parameters specific for one-step RT-PCR. The efficiency (slopes) of the target amplification and the efficiency of the reference endogenous control (GAPDH) amplification were 100% (+/−10%). Target gene expression levels were normalized to endogenous controls in all experiments. As shown in FIG. 2, Lrch4 was observed to be expressed at much higher levels than Lrch1-3. In fact, others have observed that Lrch4 is most highly expressed in human immune tissues and cells, and that this suggests that targeting it for immunomodulatory purposes may be associated with few off-target effects (see, http://biogps.gnf.org/#goto=genereport&id=4034).

Example III shRNA Inhibits Lrch4 Expression in RAW 264.7 Macrophages

In order to assess the role of Lrch 4, experiments were first conducted to determine how effectively its expression could be regulated with interfering RNA. Initially, a murine lentiviral set of 5 shRNA against murine Lrch4 was purchased from Open Biosystems/Thermo-Fisher (Huntsville, Ala.). Two of the five shRNA were determined to be most effective; the hairpin sequences of those shRNAs and the negative control (scrambled shRNA) are as follows:

```
A3 (TRCN0000121334):
                                       (SEQ ID NO: 1)
CCGGGCTCTCAAGTCTCGGAAGAATCTCGAGATTCTTCCGAGACTTGAGA

GCTTTTTG

A5 (TRCN0000121336):
                                       (SEQ ID NO: 2)
CCGGCCTTCTGAATTAAGCCTTGTACTCGAGTACAAGGCTTAATTCAGAA

GGTTTTTG

Scrambled shRNA:
                                       (SEQ ID NO: 4)
CCTAAGGTTAAGTCGCCCTCGCTCGAGCGAGGGCGACTTAACCTTAGG
```

Figure 3:
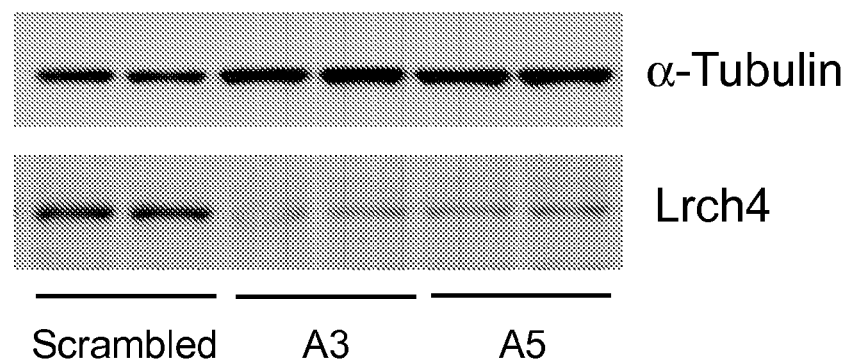
FIGS. 3(a) and (b) show shRNA-mediated reductions in Lrch4 expression, relative to α-tubulin or GAPDH expression, respectively, in RAW 264.7 macrophages.
Figure 3:
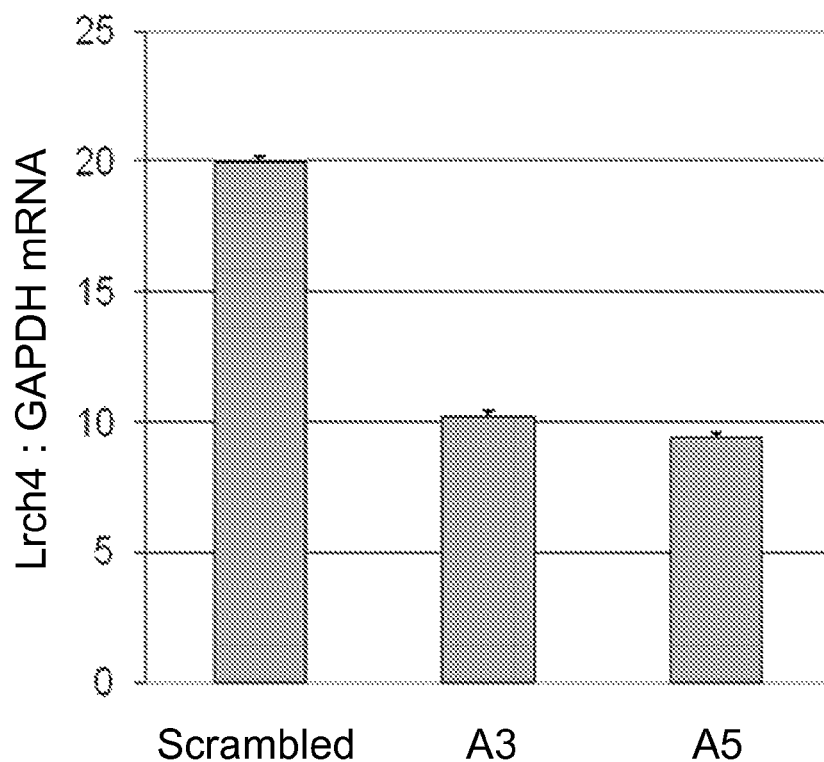

FIGS. 3(a) and (b) show shRNA-mediated reductions in Lrch4 expression, relative to α-tubulin or GAPDH expression, respectively, in RAW 264.7 macrophages. To assess the levels of Lrch4 expression in RAW 264.7 macrophages after knockdown a TaqMan probe based real-time Reverse Transcriptase PCR was used. Predeveloped, validated TaqMan primer/probe sets for murine Lrch4 (Mm00461397_m1) and GAPDH (Mm99999915_g1) were purchased (Applied Biosystems, Foster City, Calif.). Total RNA was extracted from cells with RNeasy kits (Qiagen) according to the manufacturer's protocol. DNase treatment of the RNA was performed with DNase Set (Qiagen) to remove residual DNA before reverse transcriptase (RT) PCR. RT-PCR mixtures were composed of the following: Universal PCR Master Mix, No AmpErase® (Applied Biosystems), manufacturer recommended amount of predeveloped primer/probe sets, 0.05 to 0.5 µg RNA, 0.4 U/µl RNase inhibitor (Roche Diagnostics), and 0.4 U/µl murine leukemia virus RT (Roche). Negative controls, consisting of all components except for RT enzyme, gave no signal in every case. Reactions were run in duplicate on an ABI Prism 7900HT with thermal cycling parameters specific for one-step RT-PCR. The efficiency (slopes) of the target amplification and the efficiency of the reference endogenous control (GAPDH) amplification were 100% (+/−10%). Target gene expression levels were normalized to endogenous controls in all experiments.

Example IV

Lrch4 Silencing Attenuates the LPS Response by RAW 264.7 Macrophages

Figure 4:
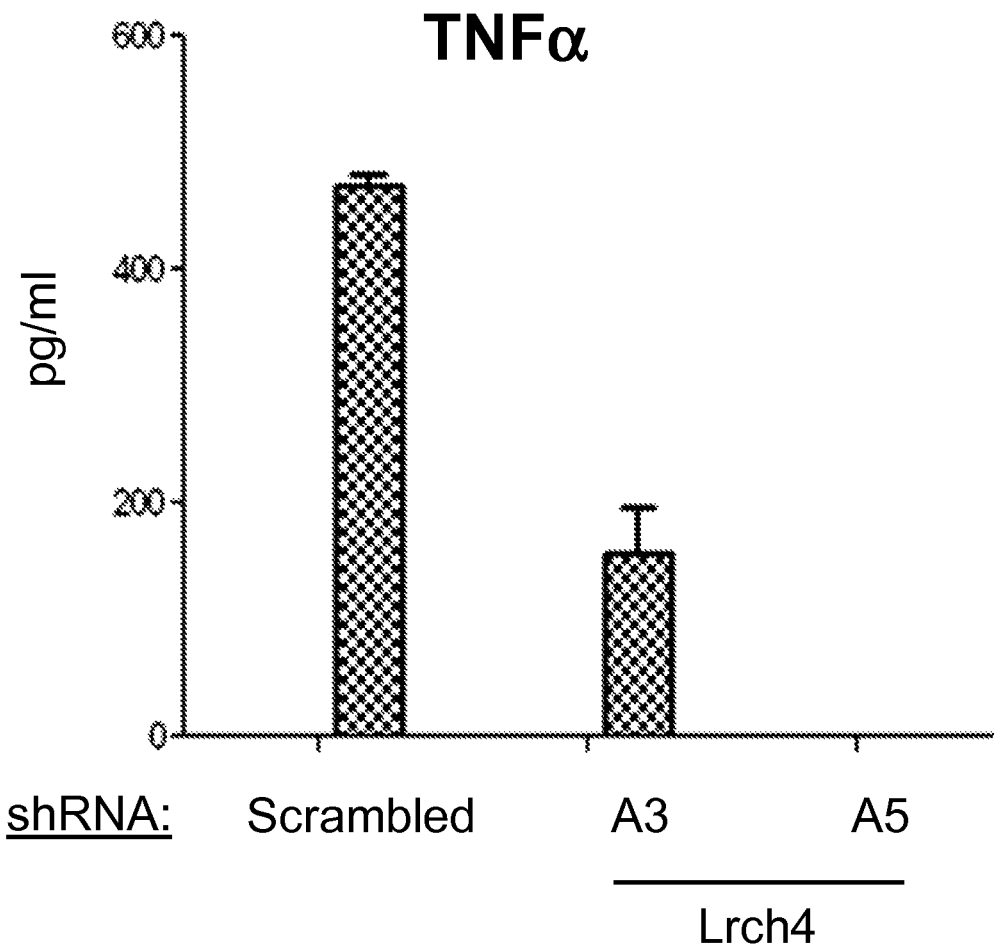
FIG. 4 illustrates the relative reduction of LPS-induced production of TNF-α by RAW 264.7 macrophages expressing Lrch4-specific shRNAs.

To assess the effect of Lrch4 silencing on the inflammatory response of macrophages, experiments were performed to determine whether TNF-α production changed when macrophages expressing Lrch4-specific interfering RNA were exposed to LPS. For these experiments, RAW264.7 cells separately transduced with the shRNAs described in example III, were plated at $0.375 \times 10^6$ cells/well of a 24 well plate and maintained under standard culture conditions overnight. The following day, the cells were washed two times with warm PBS and media was changed to complete supplemented with 100 pg/ml E. coli 0111:B4 LPS. The cells were then incubated under normal growth conditions (5% $CO_2$ at 37° C.). Following LPS exposure, cell supernatants were collected and analyzed for the presence of TNF-α using either the Bioplex multiplex bead assay (BioRad) or ELISA to TNF-α (eBioscience), per manufacturer's specifications. As shown in FIG. 4, the expression of Lrch4-specific inhibitory RNAs A3 or A5 caused a significant reduction in TNF-α expression by LPS-exposed macrophages, relative to nonspecific shRNA.

Figure 5:
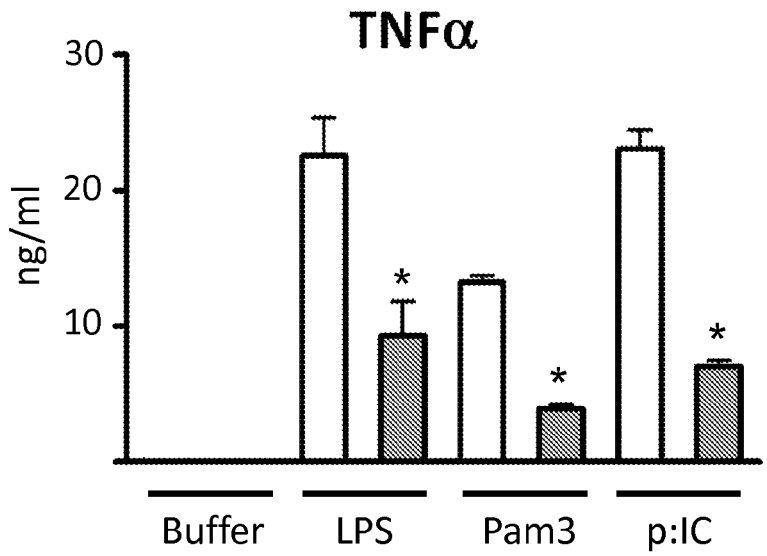
FIGS. 5(a) and (b) illustrate the relative reduction of LPS-induced production of either TNF-α (a) or G-CSF (b) by RAW 264.7 macrophages expressing Lrch4-specific inhibitory RNAs.
Figure 5:
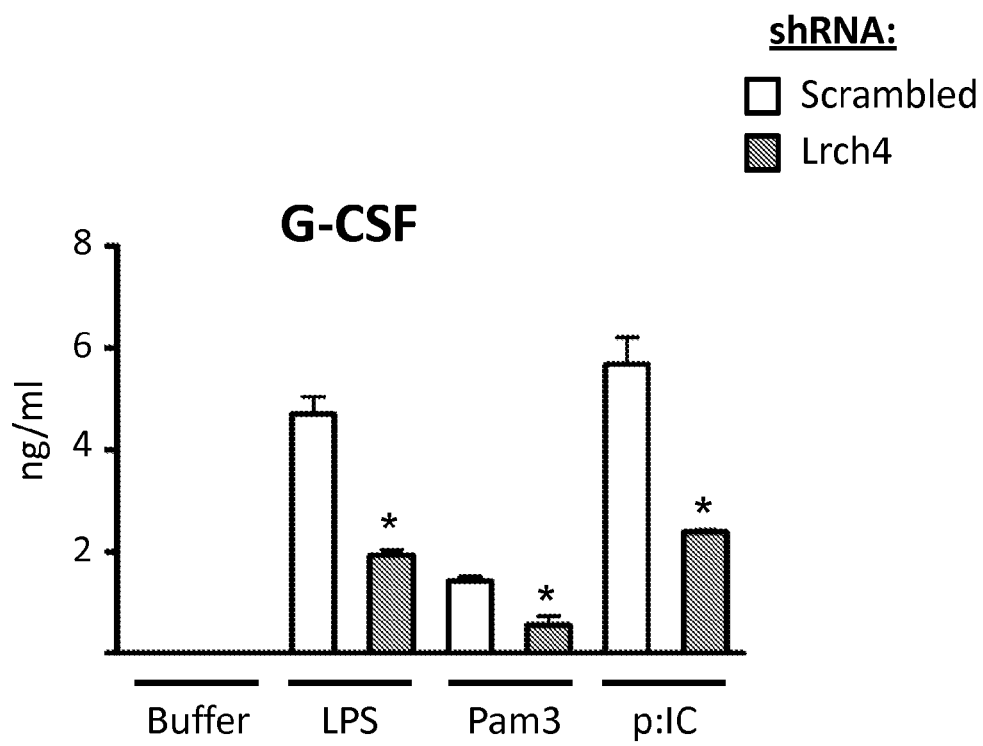
Figure 6:
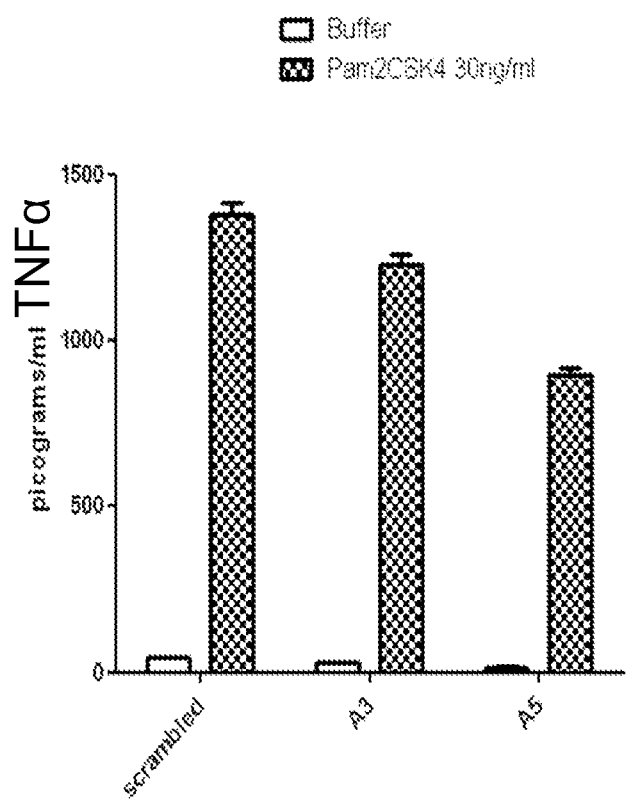
FIG. 6 illustrates the relative reduction of Pam2CSK4-induced production of TNF-α by RAW 264.7 macrophages expressing Lrch4-specific shRNAs.
Figure 7:
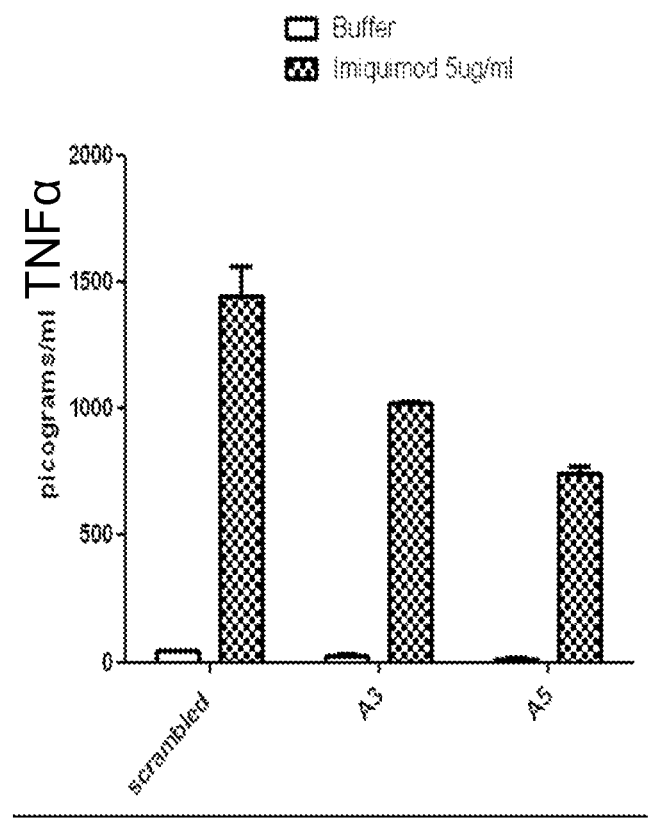
FIG. 7 illustrates the relative reduction of imiquimod-induced production of TNF-α by RAW 264.7 macrophages expressing Lrch4-specific shRNAs.

Similar experiments were conducted with ligands for different TLRs. FIG. 5 illustrates the relative reduction of Pam2CSK4-induced production of TNF-α by RAW 264.7 macrophages expressing Lrch4-specific shRNAs. FIG. 6 shows the relative reduction of imiquimod-induced production of TNF-α by RAW 264.7 macrophages expressing Lrch4-specific shRNAs. FIG. 7 depicts the relative reduction of ODN2395-induced production of TNF-α by RAW 264.7 macrophages expressing Lrch4-specific shRNAs.

Example V

Lrch4 Regulates Cytokine Responses Induced by Various TLR Ligands

Figure 8:
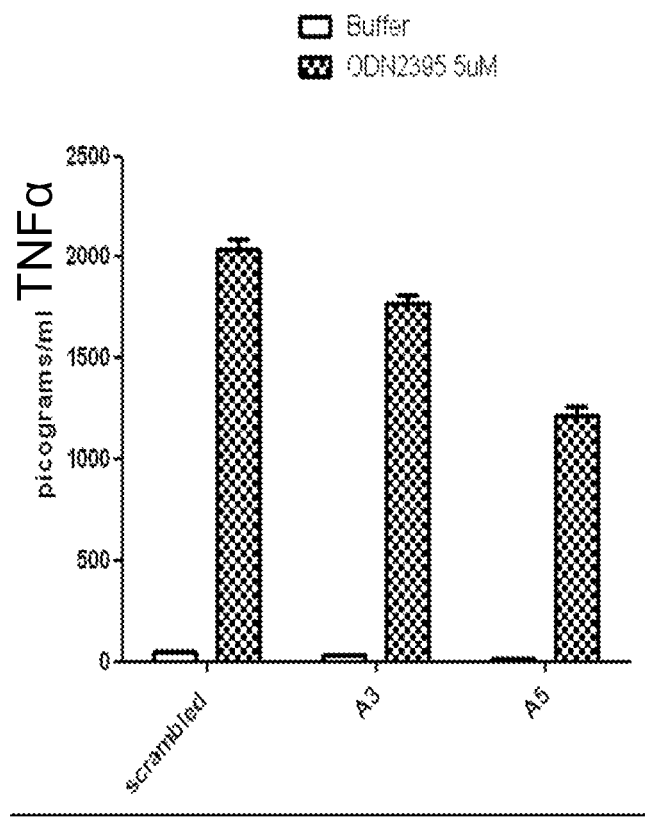
FIG. 8 illustrates the relative reduction of ODN2395-induced production of TNF-α by RAW 264.7 macrophages expressing Lrch4-specific shRNAs.

Since Lrch4 silencing was able to inhibit the expression of TNF-α in LPS exposed macrophages (example IV), additional experiments were performed to determine if this also occurred for other ligands known to induce inflammation. The general experimental design was the same as that described in example IV, however, plated cells were incubated with either LPS (1 ng/ml), the TLR2/1 ligand Pam3CSK4 (10 ng/ml), or the TLR3 ligand poly(I:C) (20 µg/ml) in order to stimulate TLR-mediated cytokine production and only macrophages transduced with SEQ ID NO: 2. FIGS. 5(a) and 8(b) show that neither TNF-α or G-CSF was produced in the absence of a stimulating ligand (buffer). Conversely, macrophages exposed to TLR ligands expressed TNF-α or G-CSF; however, in each instance, macrophages transduced with Lrch4-specific inhibitory RNA produced less cytokine that those transduced with nonspecific inhibitory RNA. Similar results were also observed for TLR2/6 ligand Pam2CSK4 (30 ng/ml), TLR7 ligand imiquimod (5 µg/ml), and TLR9 ligand ODN2395 (5 µM), as shown in FIGS. 6, 7, and 8, respectively.

Since Lrch4 silencing was observed to consistently inhibit the expression of TLR-mediated cytokine production, there was also interest in determining whether Lrch4 overexpression would increase TLR-mediated cytokine production. To accomplish this Lrch4 expression constructs were produced. In one instance a murine Lrch4 expression plasmid was made using a pCMV6-murine Lrch4 expression plasmid obtained from Origene. Using PCR, the open reading frame for murine Lrch4 was subcloned into pcDNA3.1 vector either in untagged, N-terminally HA tagged or C-terminally Flag-tagged form. A pCMV6-AC-GFP expression plasmid for human Lrch4 was obtained from Origene. Linearized and purified empty vector, untagged-Lrch4, HA-Lrch4 and Lrch4-Flag plasmids were transfected into separate RAW264.7 cells using FuGENE® HD reagent (Roche) as per manufacturer's instructions. After 48 hours the cells were plated at 20% confluence in 150 mM dishes and selected using 400 µg/ml of Geneticin® for two weeks (with fresh media every third day). Aliquots of selected cells were frozen and the remainder was maintained under selection for use in experiments.

Figure 9:
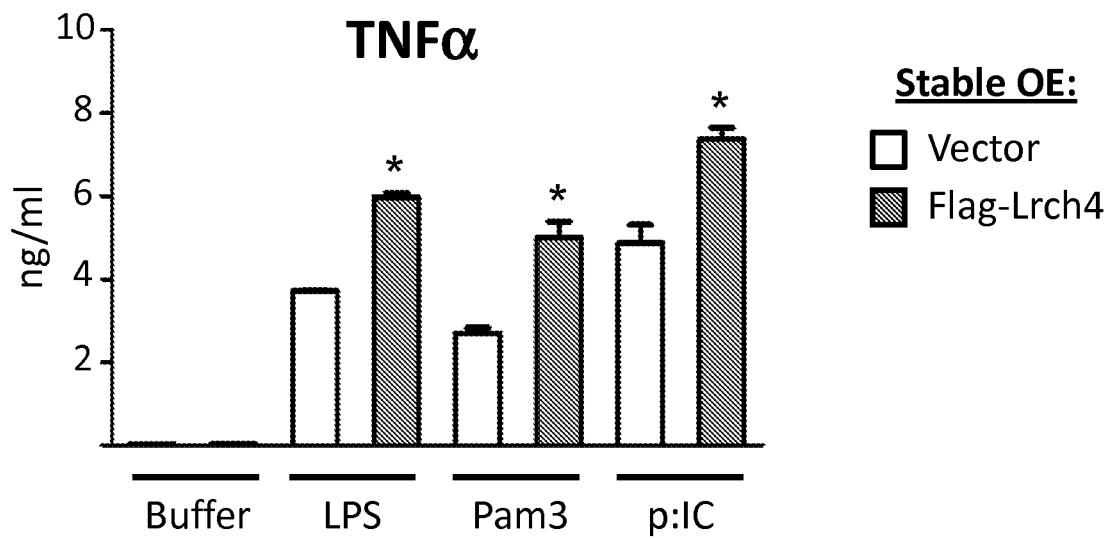
FIG. 9 shows that overexpression of Flag-tagged Lrch4 in RAW264.7 macrophages increases the production of TNF-α in response to stimulation by LPS, Pam3CSK4, or poly(I:C).
Figure 10:
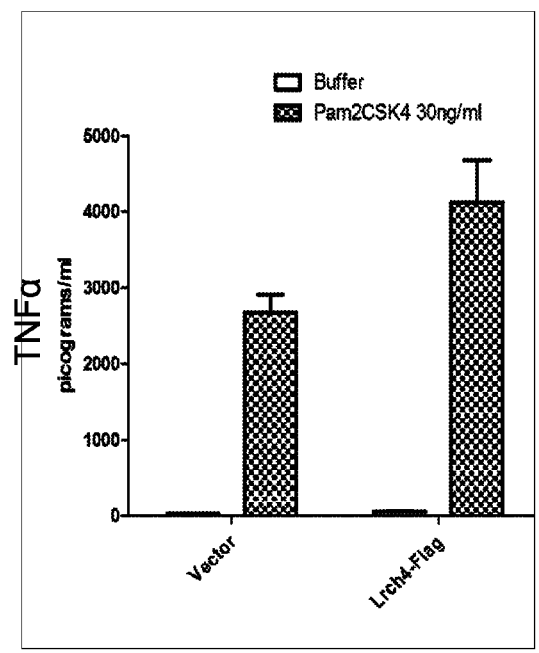
FIG. 10 shows that overexpression of Flag-tagged Lrch4 in RAW264.7 macrophages increases the production of TNF-α in response to stimulation by Pam2CSK4.
Figure 11:
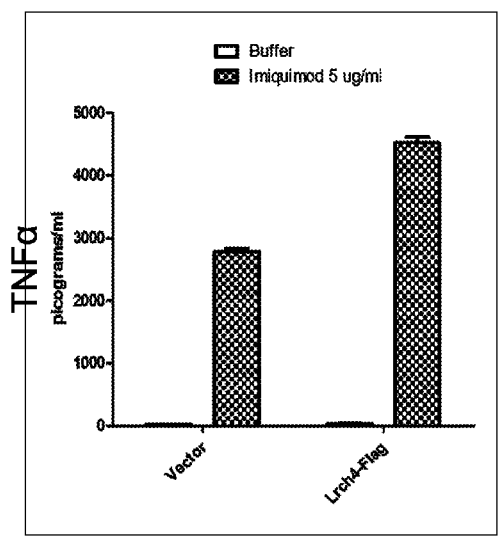
FIG. 11 shows that overexpression of Flag-tagged Lrch4 in RAW264.7 macrophages increases the production of TNF-α in response to stimulation by imiquimod.

RAW264.7 transfected with either a vector encoding murine Flag-Lrch4 or empty vector were cultured in the presence or absence of TLR ligands: LPS (1 ng/ml), Pam3CSK4 (10 µg/ml), poly(I:C) (20 ng/ml), Pam2CSK4 (30 ng/ml), or imiquimod (5 µg/ml). As shown in FIGS. 9, 10, and 11 Lrch4 overexpression had a direct correlation with increased TLR-mediated cytokine production.

Example VI

Lrch4 Silencing Attenuates the LPS Response in Human Cells

Figure 12:
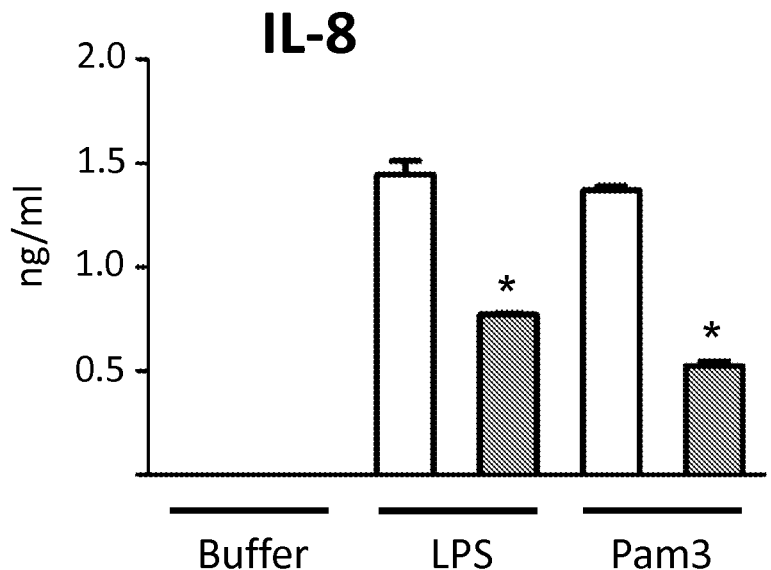
FIG. 12(a) shows reduced production of cytokine IL-8 by TLR-transfected 293-hMD2-CD14 cells expressing Lrch4-specific inhibitory RNAs following stimulation with LPS or Pam3CSK4. As depicted in FIG. 12(b), Lrch4-specific siRNA did not inhibit production of IL-8 in the presence of TNFα, which was used a negative control.
Figure 12:
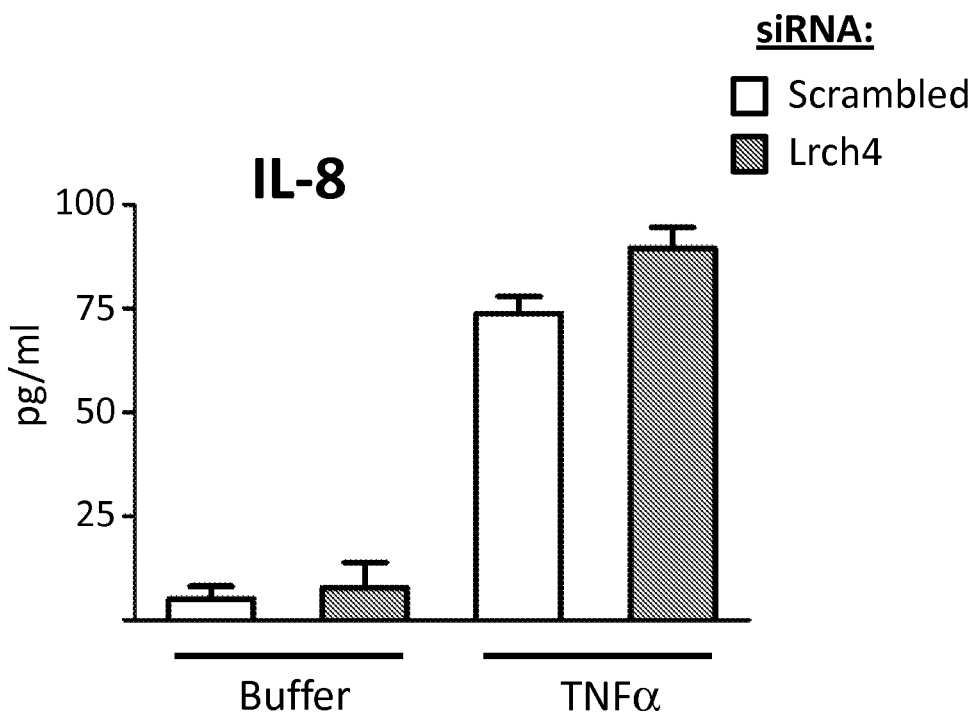

To investigate the ability of Lrch4 silencing to inhibit TLR-mediated cytokine production by human cells, interfering RNA experiments were performed using TLR-transfected 293-hMD2-CD14 cells (Invivogen). In this case, an siRNA knockdown approach was used. Lrch4-specific siRNA (Silencer(R) Select siRNA for human Lrch4, ID: s8276 [catalog #: 4392420]) GTCTGGAAATGAGTCAACA (SEQ ID NO: 3) or negative control siRNA (Silencer Negative Control #1 siRNA [catalog #: AM4611]) were transfected into the cells using Lipofectamine 2000 (Invitrogen, Carlsbad, Calif.) per manufacturer's instructions, in serum-free OptiMEM (Gibco-Invitrogen, Carlsbad, Calif.). Transfected cells (48 hrs post-transfection) were then cultured in the presence of TNF-α (negative control), LPS, or Pam3CSK4 and, following incubation, IL-8 secretion was assessed by ELISA. As depicted in FIGS. 12(a) and (b), Lrch4-specific siRNA inhibited the production of IL-8 in the presence of TLR ligands LPS and Pam3CSK4.

Example VII

Lrch4 Silencing Attenuates LPS-Mediated NF-kB Activation

Figure 13:
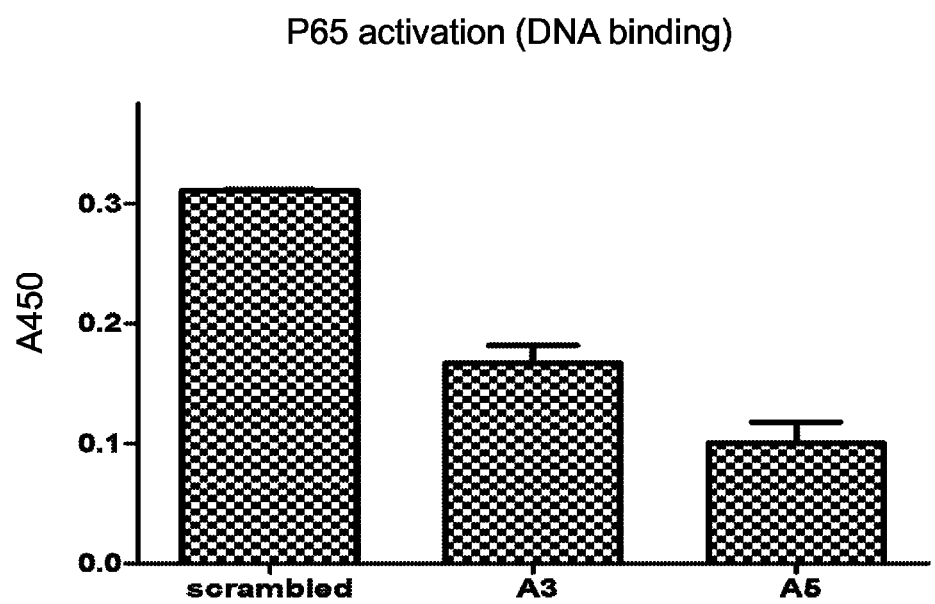
FIG. 13 depicts baseline-corrected LPS induced p65 binding in RAW 264.7 cells expressing Lrch4-specific shRNA. In both instances, NF-kB activation was reduced by the expression of Lrch4-specific shRNA.

Nuclear extracts were isolated using the NE-PER kit (Pierce) per manufacturer's instructions after buffer or LPS (1 ng/ml, 15 minutes) exposure of RAW 264.7 cells that had been transduced with either A5 Lrch4 shRNA or scrambled shRNA. Equal nuclear protein aliquots (determined by Bradford assay) were analyzed with the TransAM NF-κB p65 kit (Active Motif) per manufacturer's instructions. FIG. 13 depicts baseline-corrected LPS induced p65 binding (i.e., LPS signal minus buffer signal), which indicates that LPS-induced NF-κB activation was inhibited by the expression of Lrch4-specific shRNA.

Example VIII

Lrch4 Silencing Attenuates LPS Activation of Mitogen-Activated Protein Kinases

Figure 14:
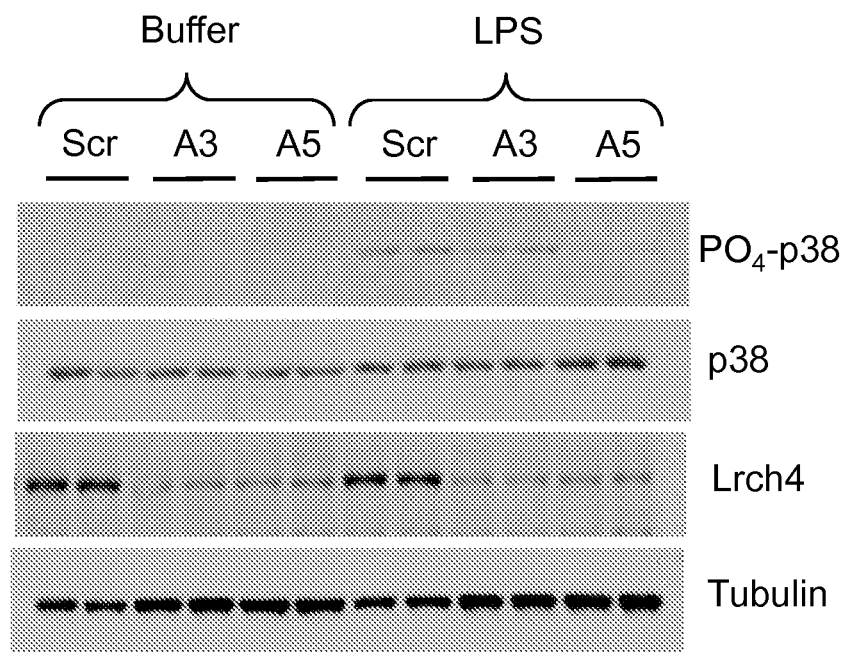
FIG. 14 is a western blot showing relative levels of phosphorylated p38, unphosphorylated p38, Lrch4, and tubulin in RAW 264.7 macrophages with, or without, LPS stimulation.

Mitogen-activated protein kinases (MAPKs), such as p38 MAPK, are known to transmit early signals into immune cells upon exposure of the cell to LPS. In order to determine whether Lrch4 regulates acute activation (i.e., phosphorylation) of MAPKs by LPS, an experimental design similar to Example IV was followed. RAW 264.7 macrophages pretreated with either scrambled, A3, or A5 Lrch4 shRNA were exposed to 1 ng/ml LPS for 15 minutes, and then equal protein aliquots (Bradford assay) of whole cell lysate were analyzed by Western blot, using standard procedures. Lysates were probed with Lrch4-specific antibodies that were custom-made for this study, PO4-p38 (Cell Signaling Technology), p38 (Santa Cruz Biotechnology), or tubulin (Santa Cruz Biotechnology). As shown in FIG. 14, Lrch4 knockdown by A5 shRNA markedly attenuates LPS-induced p38 activation; a lesser attenuation in p38 activation was also observed for A3 shRNA. These findings complement those shown in Example VII, together indicating that Lrch4 regulates early signaling events triggered by LPS in the macrophage.

Example IX

MyD88 Co-Immunoprecipitates Lrch4 from Macrophage Lysates

Figure 15:
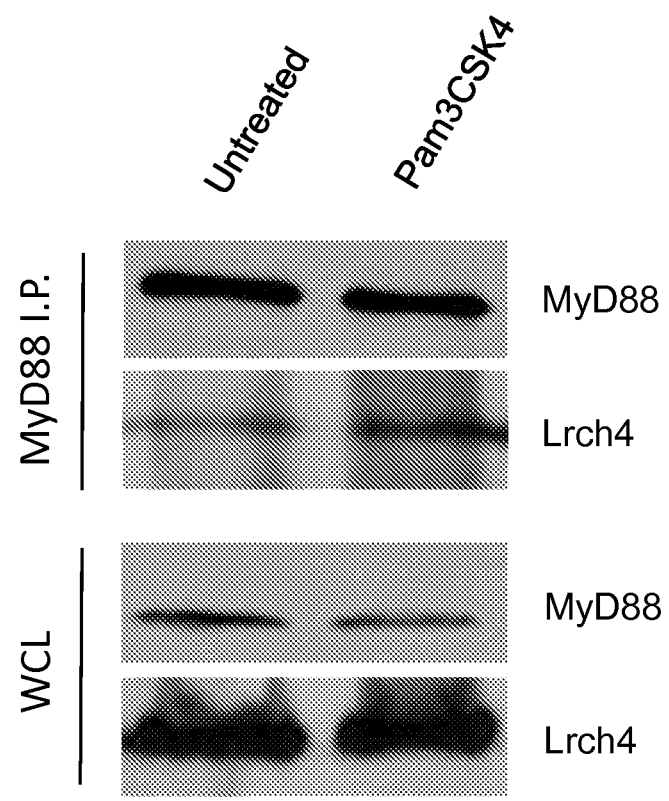
FIG. 15 shows western blot results of MyD88-Lrch4 co-immunoprecipitation from untreated or Pam3CSK4-stimulted RAW 264.7 macrophages cells. The blot shows the presence of MyD88 or Lrch4 in either whole cell lysate (WCL) or recovered using MyD88-specific antibodies.

Upon activation, all TLRs other than TLR3 transduce signals into the cell via physical association with the cytosolic adaptor protein MyD88. Given the confirmation provided by the results of Example I, that Lrch4 is localized to the cell membrane, and the finding presented in Examples VII and VIII, that Lrch4 regulates very early (15 minute) signaling events, experiments were conducted to determine whether Lrch4 physically associates with membrane-proximal proteins in TLR signaling pathways, such as MyD88. To this end, MyD88 was immunoprecipitated from untreated or Pam3CSK4-treated (100 ng/ml, 15 minutes) RAW 264.7 macrophages. After exposure, cells were washed, lysed in standard RIPA lysis buffer supplemented with protease inhibitors, and clarified by centrifugation. Whole cell lysates were then treated overnight (~16 hrs, 4° C.) with 2.5 ug/500 μl rabbit anti-MyD88 antibody (Millipore). Immunocomplexes were subsequently precipitated with protein A/G-sepharose (Santa Cruz), washed several times with ice-cold RIPA lysis buffer, and then eluted with Laemmli buffer supplemented with 20 mM DTT, followed by boiling (7 minutes). Eluates were resolved by 10% SDS-PAGE, and evaluated by standard Western blotting procedures. As shown in FIG. 15, Lrch4 is detected in MyD88 immunoprecipitates, suggesting physical association between the two proteins. Of note, Lrch4 association with MyD88 is increased in Pam3CSK4-treated cells, suggesting that physical association between the two proteins is enhanced by exposure of the cells to TLR2 ligand.

Example X

Lrch4 Interfering RNA Attenuates IL-8 Production by Constitutively Active MyD88

Figure 16:
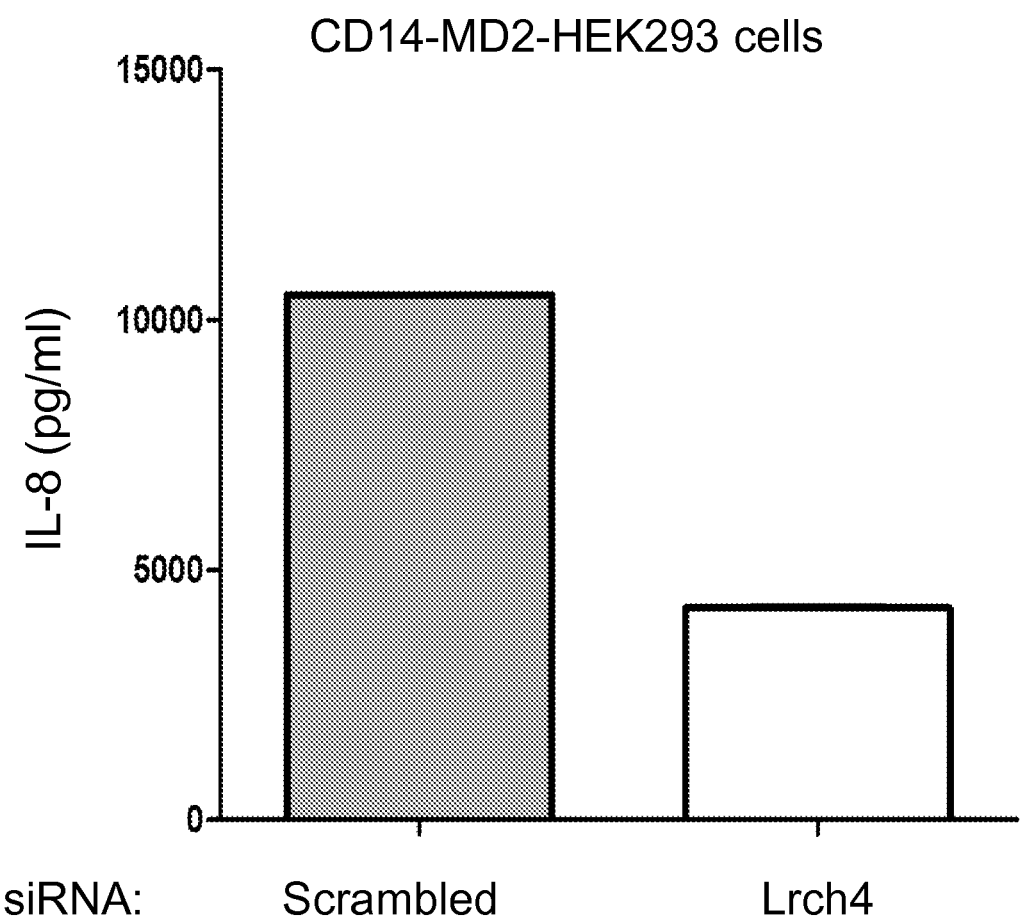
FIG. 16 illustrates levels of IL-8 produced by 293-hMD2-CD14 cells expressing constitutively active MyD88 in the presence or absence of Lrch4-specific siRNA.

Given the findings that Lrch4 physically associates with MyD88 (Example IX), and that Lrch4 regulates early signaling events that are thought to be MyD88-dependent (Examples VII, VIII), experiments were conducted to determine whether Lrch4 could be to regulate MyD88-dependent signaling in a more direct fashion. To this end, 293-hMD2-CD14 cells (Invivogen) that had been transfected with negative control siRNA or Lrch4-specific siRNA, as described in Example VI, were subsequently transfected with a plasmid for a constitutively active (CA) form of MyD88 (obtained from Dr. Jurg Tschopp, University of Lausanne). This CA MyD88 has been previously confirmed to drive cytokine induction in cells in a ligand-independent fashion; the use of non-TLR expressing HEK293 cells in these experiments (HEK293 cells do not express TLR2 or TLR4 and are unresponsive to TLR2 and TLR4 ligands) moreover excludes confounding effects from possible contaminating TLR2 or TLR4 ligands (eg, LPS). Conditioned media from the cells was harvested 6 hours following transfection with CA MyD88, and assayed by ELISA (eBioscience) for IL-8 concentration. As shown in FIG. 16, Lrch4 silencing significantly reduced IL-8 induction by CA MyD88, confirming that Lrch4 regulates MyD88-dependent signaling, and also suggesting that Lrch4 can regulate MyD88 signaling in a fashion that is independent of TLR ligands. As MyD88 is also known to play an essential role in pro-inflammatory signaling induced by the cytokines IL-1 and IL-18, these results suggest that Lrch4 may also regulate cellular responses to these cytokines. As IL-1 and IL-18 are themselves induced by TLR ligands and are thought to amplify inflammation, these results indicate the potential that Lrch4 inhibition may reduce inflammation not only through reducing cytokine production but also through attenuating cytokine effects.

Example XI

Lrch4 does not Regulate Cell Surface TLR4

Figure 17:
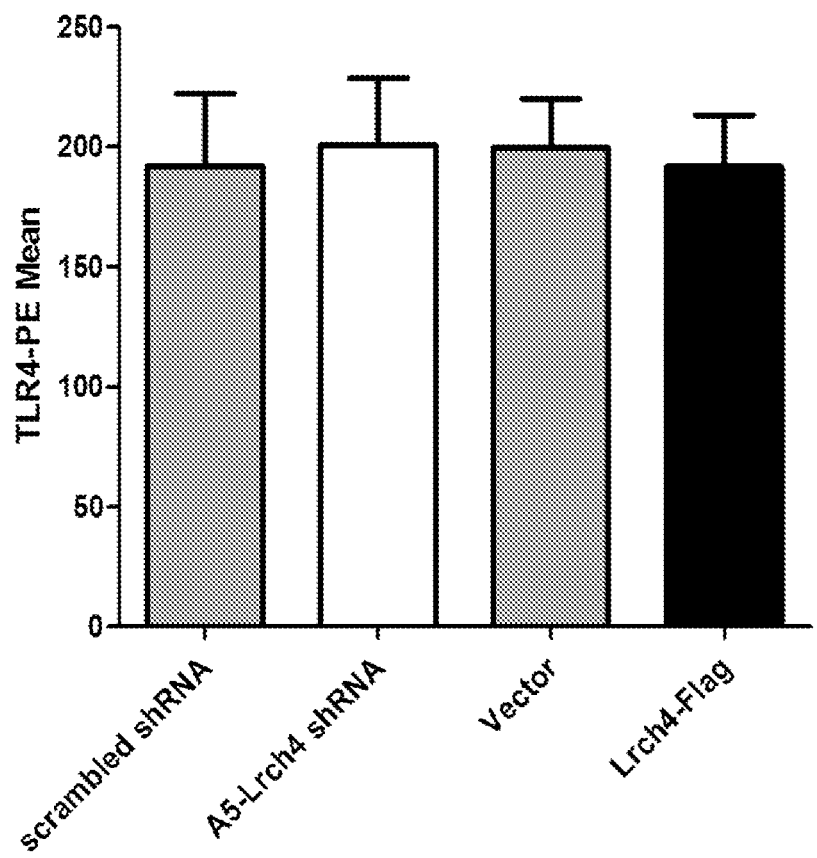
FIG. 17 depicts the relative levels of TLR4 expressed on the cell surface of RAW 264.7 cells in the presence of non-specific shRNA (scrambled shRNA), Lrch4-specific shRNA (A5-Lrch4 shRNA), empty vector (c), and Lrch4-Flag (Lrch4 overexpression).

In order to address whether Lrch4 regulates expression of TLR4 on the cell-surface, standard flow cytometry procedures were performed to quantify cell surface display on RAW 264.7 cells of TLR4 (PE-anti-TLR4 antibody, [eBioscience]) in the setting of Lrch4 silencing (A5 shRNA) as well as overexpression (Lrch4-FLAG). To ensure specificity of the antibody signal for TLR4, an isotype control antibody (PE-IgG1 K isotype control [eBioscience]) was used in parallel. As shown in FIG. 17, neither Lrch4 silencing nor overexpression alters TLR4 expression on the cell surface. These findings suggest that Lrch4 regulates the TLR4 pathway through a mechanism other than control of subcellular trafficking of TLR4 to its sentinel location on the cell surface.

Example XII

Figure 18:
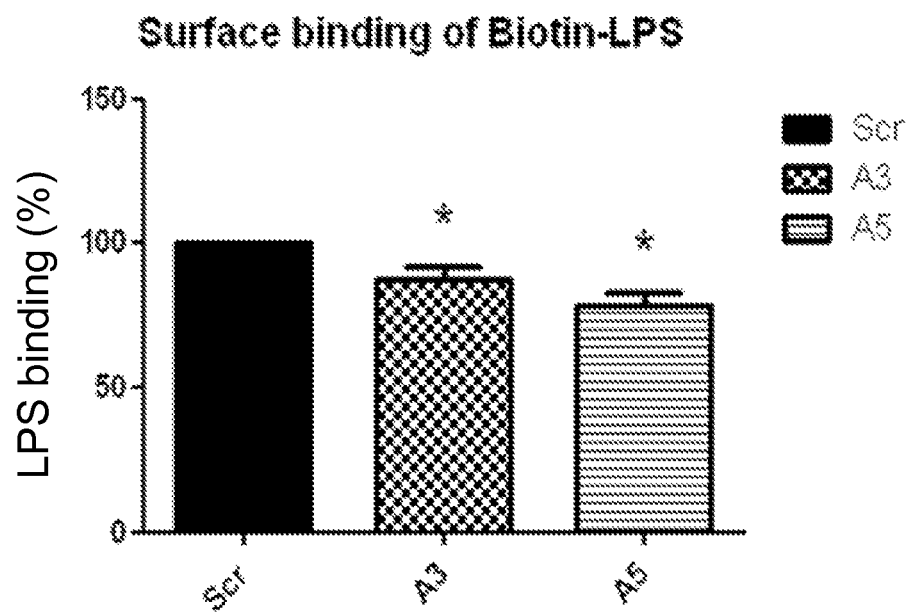
FIG. 18 shows the percent change in relative binding of biotin-labeled LPS to the surface of RAW 264.7 in the presence of Lrch4-specific shRNAs.

Lrch4 Knockdown Attenuates Binding of LPS to Cell Surface of RAW 264.7 Macrophages Experiments were conducted to assess whether inhibition of Lrch4 expression affects binding of LPS to cells. RAW 264.7 macrophages stably expressing either Lrch4-specific shRNA or scrambled shRNA were incubated with biotin-conjugated LPS for 15 minutes at 37° C. and then labeled with streptavidin-allophycocyanin (APC). Following labeling, surface-bound LPS was assessed by by flow cytometry. As shown in FIG. 18, both Lrch4-specific shRNAs A3 and A5 inhibited binding of biotin-labeled LPS to RAW 264.7 cells.

Example XIII

Lrch4 and CD14 Co-Precipitate with Biotin-LPS Pulldown of RAW 264.7 Cells

Figure 19:
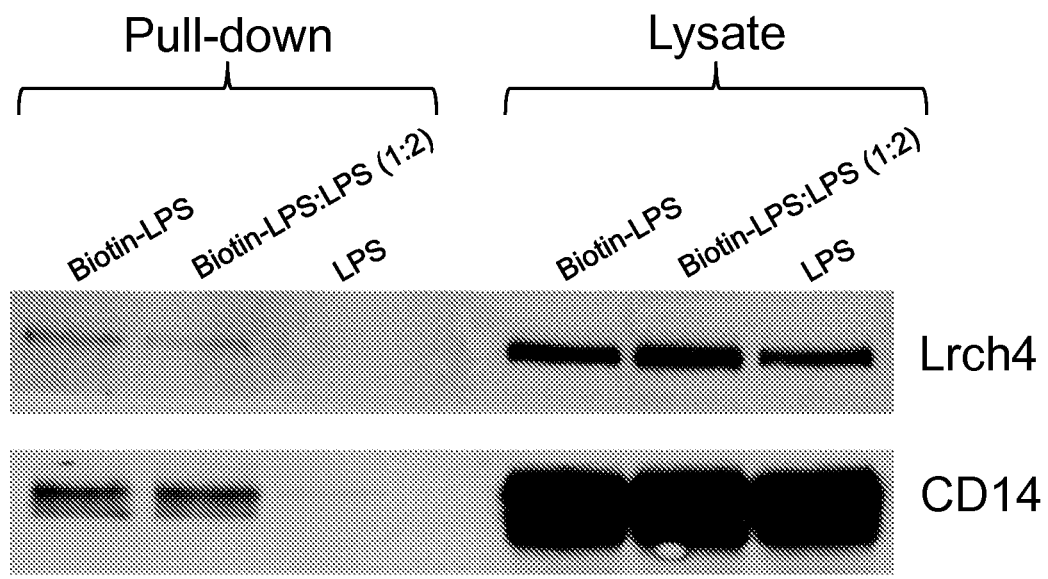
FIG. 19 depicts a Western blot showing co-precipitation of Lrch4 and CD14 from cells exposed to biotin-labeled LPS, and then affinity precipitated with streptavidin-agarose.

Co-immunoprecipitation studies were undertaken to assess the ability of Lrch4 to associate with cell-surface proteins involved in LPS binding. For these experiments, RAW 264.7 macrophages were incubated (15 minutes at 37° C.) with either 10 µg of biotin-labeled LPS, 10 µg of biotin-labeled LPS plus 20 µg LPS 10, or 10 µg of LPS alone. Following incubation, biotin-LPS was pulled down by streptavidin-sepharose. Captured complexes were washed and proteins were eluted from the sepharose and probed for Lrch4 and CD14, in parallel with probing of whole cell lysate. As shown in FIG. 19, biotin-LPS co-precipitated Lrch4 and CD14.

Example XIV

Figure 20:
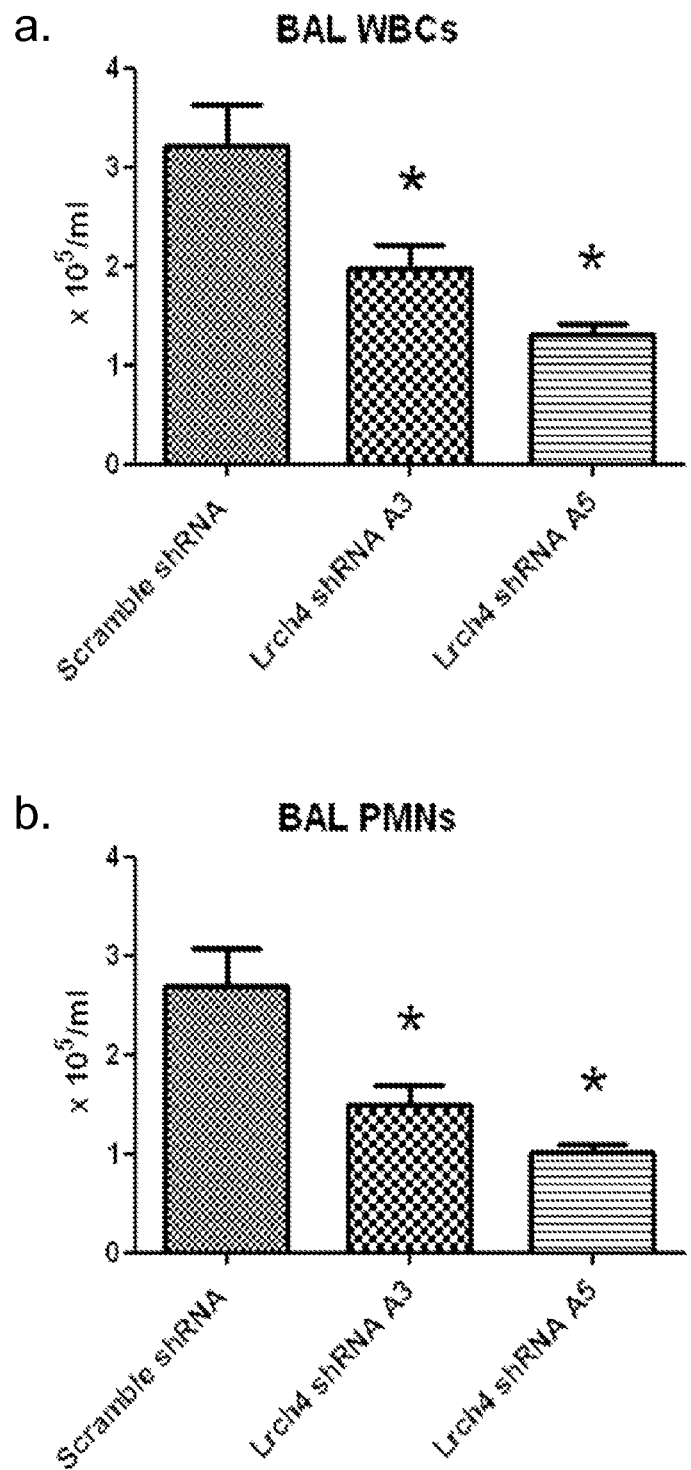
FIG. 20 shows the reduction in (a) white blood cells (WBCs) or (b) neutrophils (PMNs) present in the lung airspaces of mice treated with Lrch4-specific shRNA prior to exposure to aerosolized LPS.

Lentiviral shRNA Knockdown of Lrch4 in Murine Lungs Attenuates LPS-Induced Airway Inflammation In Vivo Mouse studies were conducted to determine whether Lrch4-specific shRNAs could reduce the effects of LPS in vivo. For these studies lentivirus encoding Lrch4-specific shRNA (A3 or A5, as indicated in FIG. 20) or non-specific shRNA (scramble) were delivered (6×10⁷ TU in 50 µl) to the lungs of C57BL/6 mice by oropharyngeal aspiration. Five days after delivery, mice were subjected to inhalation of aerosolized LPS (300 µg/ml for 30 min). Bronchoalveolar lavage (BAL) was collected 24 h later, and total white blood cells (WBCs) or neutrophils (PMNs) were quantified. As shown in FIG. 20, mice exposed to either Lrch4-specific shRNA exhibited a reduction in WBCs and PMNs following exposure to aerosolized LPS.

```
Lrch4 Protein Sequence
                                         (SEQ ID NO: 5)
MAAAVAGPLAAGGEEAAASVSLPGSPGLPGSRSAERALEEAVATGTLNLS

NRRLKHFPRGAARSYDLSDITQADLSRNRFPEVPEAACQLVSLEGLSLYH

NCLKCLNPALGNLTALTYLNLSRNQLSSLPPYICQLPLRVLIISNNKLGA

LPPDISTLGSLRQLDVSSNELQSLPVELCSLRSLRDLNVRRNQLSTLPDE

LGDLPLVRLDFSCNRISRIPVSFCRLRHLQVVLLDSNP

LQSPPAQICLKGKLHIFKYLTMEAGRRGAALGDLVPSRPPSFSPCPAEDL

FPGRRYDGGLDSGFHSVDSGSKRWSGNESTDDFSELSFRISELARDPRGP

RQPREDGAGDGDLEQIDFIDSHVPGEDEDRSAAEEQLPSELSLVAGDVEK

PSSSRREEPAGEERRRPDTLQLWQERERKQQQQSGGWGSPRKDSVLKRGI

RAAGAGASAPSTQATCNGPPKSSTTQLGVSGGQGAPTPPPTSQDPLPVSG

PVTAPVPRPLGSIQRPNSFLFRSSSQSGSSPSSPESVLRPRPFPQEKELI

SQLRQVLESRLQQPLPEDLAEALANGVLLCQLANQLRPRSVPFIHVPSPA

VPKLSALKSRKNVESFLEACRKMGVPEADLCSPSDLLRGTAQGLQTVLEA

VILVGGKAPLPVQPSSGLGGFLLFYVVFMLLLYVVYTRLLGS

Lrch4 Nucleotide Sequence
                                         (SEQ ID NO: 6)
ATGGCGGCAGCAGTAGCGGGCCCACTCGCCGCCGGGGGTGAGGAAGCTGC

AGCTTCAGTGTCCTTGCCAGGGTCTCCTGGTCTACCTGGGAGCCGTAGCG

CAGAACGAGCCCTAGAGGAGGCTGTGGCCACCGGGACCCTGAACTTGTCC

AACCGGCGTTTGAAGCACTTCCCCCGGGGCGCGGCCCGCAGTTACGACTT

GTCAGACATCACCCAGGCTGACTTGTCTCGGAACCGGTTTCCCGAGGTGC

CTGAGGCAGCTTGCCAGCTGGTGTCCCTGGAAGGCCTGAGCCTCTACCAC

AATTGCCTGAAATGCCTGAACCCAGCCTTGGGGAATCTTACAGCCCTCAC

CTACCTCAACCTCAGCCGGAACCAGCTGTCGTCGTTGCCACCCTACATCT

GCCAGCTGCCCCTTCGAGTGCTTATCATCAGCAACAACAAGTTAGGAGCC

CTGCCTCCAGACATCAGCACCTTGGGAAGCCTGCGGCAGCTTGATGTGAG

CAGCAATGAGCTGCAGTCCCTGCCCGTGGAGCTGTGTAGCCTCCGTTCCC

TGCGGGATCTCAATGTTCGAAGGAACCAGCTCAGTACCCTGCCTGATGAG

CTGGGAGACCTTCCTCTGGTCCGCCTGGATTTCTCCTGTAACCGCATCTC

CCGAATCCCCGTCTCCTTCTGCCGCCTCAGGCACCTGCAGGTCGTTCTGC

TGGATAGCAACCCCCTACAGAGTCCACCTGCCCAGATATGCCTGAAGGGG

AAACTTCACATCTTCAAGTACCTAACAATGGAAGCTGGCCGGAGGGGAGC

CGCCCTCGGGGACCTGGTCCCTTCCCGCCCCCCAAGTTTTAGTCCTTGCC

CTGCCGAAGATTTATTTCCGGGACGTCGTTATGATGGTGGCCTGGACTCA

GGCTTCCACAGCGTTGACAGTGGCAGCAAGAGGTGGTCAGGAAATGAGTC

CACAGATGATTTTTCAGAGCTGTCTTTCCGGATCTCGGAGCTGGCTCGTG

ATCCCCGGGGGCCTAGACAACCTAGGGAAGATGGCGCTGGCGATGGAGAC

CTGGAGCAGATTGACTTTATTGACAGCCACGTTCCTGGGGAAGATGAAGA

TCGAAGTGCAGCTGAGGAGCAGCTGCCTTCTGAATTAAGCCTTGTAGCAG

GGGATGTGGAGAAGCCATCTAGCAGCAGGCGAGAGGAGCCTGCAGGGGAG

GAGAGGCGGCGCCCAGACACTTTGCAGTTGTGGCAGGAACGGGAGCGGAA

GCAACAGCAACAGAGTGGGGGATGGGGGTCCCCCAGGAAGGACAGCGTCC

TGAAGCGGGGGATCCGAGCTGCCGGGGCAGGTGCTTCGGCCCCATCCACA

CAGGCCACCTGCAATGGCCCACCAAAGTCCAGCACTACCCAACTGGGAGT

TTCAGGGGGGCAGGGAGCTCCCACACCACCCCCCACCTCCCAGGACCCCC

TTCCTGTATCTGGACCAGTGACAGCTCCTGTTCCCAGGCCCCTGGGCTCC

ATTCAGAGACCAAACAGCTTCCTCTTCCGGTCCTCTTCTCAGAGTGGCTC

TAGTCCTTCCTCTCCAGAGTCTGTTTTGAGACCTCGGCCGTTTCCTCAGG

AGAAGGAGCTAATATCCCAACTTCGCCAGGTCCTAGAGTCGCGGCTGCAG

CAGCCCCTACCTGAGGACCTGGCAGAAGCTCTCGCCAACGGAGTCCTCCT

TTGCCAGCTGGCGAACCAGCTGCGGCCCCGCTCTGTACCCTTCATTCATG

TGCCCTCACCTGCTGTGCCAAAGCTCAGTGCTCTCAAGTCTCGGAAGAAT

GTCGAGAGTTTCCTAGAAGCCTGTCGGAAAATGGGTGTGCCTGAGGCTGA
```

CCTGTGCTCGCCCTCGGATCTCCTCCGGGGCACCGCCCAGGGGCTGCAGA

CCGTCCTGGAGGCTGTGATCCTGGTTGGGGGCAAGGCCCCTCTCCCAGTC

CAGCCCTCCTCTGGTCTGGGTGGCTTCCTCCTCTTCTACGTGGTCTTCAT

GCTGCTGCTCTATGTCGTCTACACTCGGCTCCTGGGCTCCTAG

---

What is claimed:

1. A method of reducing inflammation in a subject comprising reducing the expression of Lrch4 in the subject by administering a Lrch4-specific oligonucleotide to the subject.

2. The method of claim 1, wherein the inflammation is caused by sepsis.

3. The method of claim 1 wherein the Lrch4-specific oligonucleotide is an siRNA or a shRNA.

4. The method of claim 3 wherein the Lrch4-specific oligonucleotide comprises SEQ ID NO: 1, SEQ ID NO: 2, or SEQ ID NO: 3.

5. The method of claim 1, wherein reducing the expression of Lrch4 in the subject reduces the expression of at least one of TNF-α, G-CSF, IL-8, and IFN-β.

6. The method of claim 2, wherein the Lrch4-specific oligonucleotide comprises SEQ ID NO: 1, SEQ ID NO: 2, or SEQ ID NO: 3.

7. The method of claim 6, wherein sepsis is caused by exposure of a subject to an endotoxin.

8. The method of claim 7, wherein the endotoxin is lipopolysaccharides (LPS).

9. The method of claim 2, wherein sepsis is caused by exposure of a subject to an endotoxin.

10. The method of claim 9, wherein the endotoxin is lipopolysaccharides (LPS).

* * * * *

SEQUENCE LISTING

<160> NUMBER OF SEQ ID NOS: 6

<210> SEQ ID NO 1
<211> LENGTH: 58
<212> TYPE: DNA
<213> ORGANISM: Artificial Sequence
<220> FEATURE:
<223> OTHER INFORMATION: Synthetic: A3 (TRCN0000121334)

<400> SEQUENCE: 1
ccgggctctc aagtctcgga agaatctcga gattcttccg agacttgaga gcttttg        58

<210> SEQ ID NO 2
<211> LENGTH: 58
<212> TYPE: DNA
<213> ORGANISM: Artificial Sequence
<220> FEATURE:
<223> OTHER INFORMATION: Synthetic: A5 (TRCN0000121336)

<400> SEQUENCE: 2
ccggccttct gaattaagcc ttgtactcga gtacaaggct taattcagaa ggttttg        58

<210> SEQ ID NO 3
<211> LENGTH: 19
<212> TYPE: DNA
<213> ORGANISM: Artificial Sequence
<220> FEATURE:
<223> OTHER INFORMATION: Synthetic: Lrch4-specific siRNA

<400> SEQUENCE: 3
gtctggaaat gagtcaaca        19

<210> SEQ ID NO 4
<211> LENGTH: 48
<212> TYPE: DNA
<213> ORGANISM: Artificial Sequence
<220> FEATURE:
<223> OTHER INFORMATION: Synthetic: Scrambled shRNA

<400> SEQUENCE: 4
cctaaggtta agtcgccctc gctcgagcga gggcgactta accttagg        48

<210> SEQ ID NO 5
<211> LENGTH: 680
<212> TYPE: PRT
<213> ORGANISM: Homo Sapiens
<220> FEATURE:
<221> NAME/KEY: misc_feature
<223> OTHER INFORMATION: Lrch4 Protein Sequence

<400> SEQUENCE: 5

Met Ala Ala Ala Val Ala Gly Pro Leu Ala Ala Gly Gly Glu Glu Ala
1               5                   10                  15

Ala Ala Ser Val Ser Leu Pro Gly Ser Pro Gly Leu Pro Gly Ser Arg
            20                  25                  30

Ser Ala Glu Arg Ala Leu Glu Glu Ala Val Ala Thr Gly Thr Leu Asn
        35                  40                  45

Leu Ser Asn Arg Arg Leu Lys His Phe Pro Arg Gly Ala Ala Arg Ser

```
                50                  55                  60
Tyr Asp Leu Ser Asp Ile Thr Gln Ala Asp Leu Ser Arg Asn Arg Phe
 65                  70                  75                  80

Pro Glu Val Pro Glu Ala Ala Cys Gln Leu Val Ser Leu Glu Gly Leu
                 85                  90                  95

Ser Leu Tyr His Asn Cys Leu Lys Cys Leu Asn Pro Ala Leu Gly Asn
            100                 105                 110

Leu Thr Ala Leu Thr Tyr Leu Asn Leu Ser Arg Asn Gln Leu Ser Ser
            115                 120                 125

Leu Pro Pro Tyr Ile Cys Gln Leu Pro Leu Arg Val Leu Ile Ile Ser
130                 135                 140

Asn Asn Lys Leu Gly Ala Leu Pro Pro Asp Ile Ser Thr Leu Gly Ser
145                 150                 155                 160

Leu Arg Gln Leu Asp Val Ser Ser Asn Glu Leu Gln Ser Leu Pro Val
                165                 170                 175

Glu Leu Cys Ser Leu Arg Ser Leu Arg Asp Leu Asn Val Arg Arg Asn
            180                 185                 190

Gln Leu Ser Thr Leu Pro Asp Glu Leu Gly Asp Leu Pro Leu Val Arg
            195                 200                 205

Leu Asp Phe Ser Cys Asn Arg Ile Ser Arg Ile Pro Val Ser Phe Cys
210                 215                 220

Arg Leu Arg His Leu Gln Val Val Leu Leu Asp Ser Asn Pro Leu Gln
225                 230                 235                 240

Ser Pro Pro Ala Gln Ile Cys Leu Lys Gly Lys Leu His Ile Phe Lys
                245                 250                 255

Tyr Leu Thr Met Glu Ala Gly Arg Arg Gly Ala Ala Leu Gly Asp Leu
            260                 265                 270

Val Pro Ser Arg Pro Ser Phe Ser Pro Cys Pro Ala Glu Asp Leu
            275                 280                 285

Phe Pro Gly Arg Arg Tyr Asp Gly Gly Leu Asp Ser Gly Phe His Ser
290                 295                 300

Val Asp Ser Gly Ser Lys Arg Trp Ser Gly Asn Glu Ser Thr Asp Asp
305                 310                 315                 320

Phe Ser Glu Leu Ser Phe Arg Ile Ser Glu Leu Ala Arg Asp Pro Arg
                325                 330                 335

Gly Pro Arg Gln Pro Arg Glu Asp Gly Ala Gly Asp Gly Asp Leu Glu
            340                 345                 350

Gln Ile Asp Phe Ile Asp Ser His Val Pro Gly Glu Asp Glu Asp Arg
            355                 360                 365

Ser Ala Ala Glu Glu Gln Leu Pro Ser Glu Leu Ser Leu Val Ala Gly
370                 375                 380

Asp Val Glu Lys Pro Ser Ser Arg Arg Glu Glu Pro Ala Gly Glu
385                 390                 395                 400

Glu Arg Arg Arg Pro Asp Thr Leu Gln Leu Trp Gln Glu Arg Glu Arg
                405                 410                 415

Lys Gln Gln Gln Gln Ser Gly Gly Trp Gly Ser Pro Arg Lys Asp Ser
            420                 425                 430

Val Leu Lys Arg Gly Ile Arg Ala Ala Gly Ala Gly Ala Ser Ala Pro
            435                 440                 445

Ser Thr Gln Ala Thr Cys Asn Gly Pro Pro Lys Ser Ser Thr Thr Gln
450                 455                 460

Leu Gly Val Ser Gly Gly Gln Gly Ala Pro Thr Pro Pro Thr Ser
465                 470                 475                 480
```

```
Gln Asp Pro Leu Pro Val Ser Gly Pro Val Thr Ala Pro Val Pro Arg
                485                 490                 495
Pro Leu Gly Ser Ile Gln Arg Pro Asn Ser Phe Leu Phe Arg Ser Ser
            500                 505                 510
Ser Gln Ser Gly Ser Ser Pro Ser Pro Glu Ser Val Leu Arg Pro
        515                 520                 525
Arg Pro Phe Pro Gln Glu Lys Glu Leu Ile Ser Gln Leu Arg Gln Val
    530                 535                 540
Leu Glu Ser Arg Leu Gln Gln Pro Leu Pro Glu Asp Leu Ala Glu Ala
545                 550                 555                 560
Leu Ala Asn Gly Val Leu Leu Cys Gln Leu Ala Asn Gln Leu Arg Pro
                565                 570                 575
Arg Ser Val Pro Phe Ile His Val Pro Ser Pro Ala Val Pro Lys Leu
            580                 585                 590
Ser Ala Leu Lys Ser Arg Lys Asn Val Glu Ser Phe Leu Glu Ala Cys
        595                 600                 605
Arg Lys Met Gly Val Pro Glu Ala Asp Leu Cys Ser Pro Ser Asp Leu
    610                 615                 620
Leu Arg Gly Thr Ala Gln Gly Leu Gln Thr Val Leu Glu Ala Val Ile
625                 630                 635                 640
Leu Val Gly Gly Lys Ala Pro Leu Pro Val Gln Pro Ser Ser Gly Leu
                645                 650                 655
Gly Gly Phe Leu Leu Phe Tyr Val Val Phe Met Leu Leu Leu Tyr Val
            660                 665                 670
Val Tyr Thr Arg Leu Leu Gly Ser
        675                 680

<210> SEQ ID NO 6
<211> LENGTH: 2043
<212> TYPE: DNA
<213> ORGANISM: Homo Sapiens
<220> FEATURE:
<221> NAME/KEY: misc_feature
<223> OTHER INFORMATION: Lrch4 Nucleotide Sequence

<400> SEQUENCE: 6
atggcggcag cagtagcggg cccactcgcc gccggggtg aggaagctgc agcttcagtg      60
tccttgccag ggtctcctgg tctacctggg agccgtagcg cagaacgagc cctagaggag     120
gctgtggcca ccgggaccct gaacttgtcc aaccggcgtt tgaagcactt ccccgggc     180 gcggcccgca gttacgactt gtcagacatc acccaggctg acttgtctcg gaaccggttt     240
cccgaggtgc ctgaggcagc ttgccagctg gtgtccctgg aaggcctgag cctctaccac     300
aattgcctga atgcctgaa cccagccttg gggaatctta cagccctcac ctacctcaac     360
ctcagccgga accagctgtc gtcgttgcca ccctacatct gccagctgcc ccttcgagtg     420
cttatcatca gcaacaacaa gttaggagcc ctgcctccag acatcagcac cttgggaagc     480
ctgcggcagc ttgatgtgag cagcaatgag ctgcagtccc tgcccgtgga gctgtgtagc     540
ctccgttccc tgcgggatct caatgttcga aggaaccagc tcagtaccct gcctgatgag     600
ctgggagacc ttcctctggt ccgcctggat ttctcctgta accgcatctc ccgaatcccc     660
gtctccttct gccgcctcag gcacctgcag gtcgttctgc tggatagcaa ccccctacag     720
agtccacctg cccagatatg cctgaagggg aaacttcaca tcttcaagta cctaacaatg     780
gaagctggcc ggaggggagc cgccctcggg gacctggtcc cttcccgccc cccaagtttt     840
```

```
agtccttgcc ctgccgaaga tttatttccg ggacgtcgtt atgatggtgg cctggactca    900
ggcttccaca gcgttgacag tggcagcaag aggtggtcag gaaatgagtc cacagatgat    960
ttttcagagc tgtctttccg gatctcggag ctggctcgtg atccccgggg gcctagacaa   1020
cctagggaag atggcgctgg cgatggagac ctggagcaga ttgactttat tgacagccac   1080
gttcctgggg aagatgaaga tcgaagtgca gctgaggagc agctgccttc tgaattaagc   1140
cttgtagcag gggatgtgga gaagccatct agcagcaggc gagaggagcc tgcaggggag   1200
gagaggcggc gcccagacac tttgcagttg tggcaggaac gggagcggaa gcaacagcaa   1260
cagagtgggg gatgggggtc ccccaggaag gacagcgtcc tgaagcgggg gatccgagct   1320
gccggggcag gtgcttcggc cccatccaca caggccacct gcaatggccc accaaagtcc   1380
agcactaccc aactgggagt tcagggggg cagggagctc ccacaccacc ccccacctcc    1440
caggaccccc ttcctgtatc tggaccagtg acagctcctg ttcccaggcc cctgggctcc   1500
attcagagac caaacagctt cctcttccgg tcctcttctc agagtggctc tagtccttcc   1560
tctccagagt ctgttttgag acctcggccg tttcctcagg agaaggagct aatatcccaa   1620
cttcgccagg tcctagagtc gcggctgcag cagcccctac ctgaggacct ggcagaagct   1680
ctcgccaacg gagtcctcct ttgccagctg gcgaaccagc tgcggccccg ctctgtaccc   1740
ttcattcatg tgccctcacc tgctgtgcca aagctcagtg ctctcaagtc tcggaagaat   1800
gtcgagagtt tcctagaagc ctgtcggaaa atgggtgtgc ctgaggctga cctgtgctcg   1860
ccctcggatc tcctccgggg caccgcccag gggctgcaga ccgtcctgga ggctgtgatc   1920
ctggttgggg gcaaggcccc tctcccagtc cagccctcct ctggtctggg tggcttcctc   1980
ctcttctacg tggtcttcat gctgctgctc tatgtcgtct acactcggct cctgggctcc   2040
tag                                                                  2043
```